US012788983B2

(12) United States Patent
Shrivastav et al.

(10) Patent No.: US 12,788,983 B2
(45) Date of Patent: Nov. 10, 2026

(54) NEUROMODULATION TECHNIQUES TO CREATE A NERVE BLOCKAGE WITH A COMBINATION STIMULATION/BLOCK THERAPY FOR GLYCEMIC CONTROL

(71) Applicant: Medtronic, Inc., Minneapolis, MN (US)

(72) Inventors: Maneesh Shrivastav, Blaine, MN (US); ShaileshKumar V. Musley, Brooklyn Park, MN (US); Kanthaiah Koka, Valencia, CA (US); Steven M. Goetz, North Oaks, MN (US); Suryakiran Vadrevu, Santa Clarita, CA (US); Rebecca K. Gottlieb, Culver City, CA (US); David John Miller, Austin, TX (US); Leonid M. Litvak, Los Angeles, CA (US)

(73) Assignee: Medtronic, Inc., Minneapolis, MN (US)

(*) Notice: Subject to any disclaimer, the term of this patent is extended or adjusted under 35 U.S.C. 154(b) by 374 days.

(21) Appl. No.: 18/131,555

(22) Filed: Apr. 6, 2023

(65) Prior Publication Data

US 2023/0355975 A1 Nov. 9, 2023

Related U.S. Application Data

(60) Provisional application No. 63/342,998, filed on May 17, 2022, provisional application No. 63/342,967,
(Continued)

(51) Int. Cl.
*A61N 1/36* (2006.01)
*A61B 5/00* (2006.01)
(Continued)

(52) U.S. Cl.
CPC ...... *A61N 1/36053* (2013.01); *A61B 5/14532* (2013.01); *A61B 5/7435* (2013.01);
(Continued)

(58) Field of Classification Search
CPC .. A61N 1/36053; A61N 1/025; A61N 1/0507; A61N 1/0551; A61N 1/0556;
(Continued)

(56) References Cited

U.S. PATENT DOCUMENTS

| | | | |
|---|---|---|---|
| 4,602,624 | A | 7/1986 | Naples et al. |
| 4,926,874 | A | 5/1990 | Lee |

(Continued)

FOREIGN PATENT DOCUMENTS

| | | |
|---|---|---|
| CN | 101401314 | 4/2009 |
| WO | WO 2017/115368 | 7/2017 |

(Continued)

OTHER PUBLICATIONS

Aune et al. "Diabetes mellitus and the risk of sudden cardiac death: a systematic review and meta-analysis of prospective studies," Nutrition, Metabolism and Cardiovascular Diseases, 2018, vol. 28, pp. 543-556.

(Continued)

*Primary Examiner* — Carl H Layno
*Assistant Examiner* — Maria Catherine Anthony
(74) *Attorney, Agent, or Firm* — Sheridan Ross PC

(57) ABSTRACT

A system is provided herein for stimulating an anatomical element of a patient to achieve glycemic control for the patient. In some examples, the system may include a device configured to generate a current and an electrode device electrically coupled to the device that includes a plurality of electrodes configured for placement on or around the anatomical element. The device may receive instructions to apply the current to the anatomical element via the plurality
(Continued)

of electrodes of the electrode device. Additionally, the current may be applied using a first waveform of a plurality of waveforms that the device is capable of generating, where each of the plurality of waveforms comprise a substantially similar charge density. Additionally or alternatively, a system is provided that provides a pharmacological blockade at the anatomical element using a micropump that is configured to deliver a pharmacological agent to the anatomical element to achieve glycemic control.

18 Claims, 8 Drawing Sheets

Related U.S. Application Data filed on May 17, 2022, provisional application No. 63/342,945, filed on May 17, 2022, provisional application No. 63/339,049, filed on May 6, 2022, provisional application No. 63/339,101, filed on May 6, 2022, provisional application No. 63/339,024, filed on May 6, 2022, provisional application No. 63/339,304, filed on May 6, 2022, provisional application No. 63/339,136, filed on May 6, 2022, provisional application No. 63/339,154, filed on May 6, 2022, provisional application No. 63/339,160, filed on May 6, 2022, provisional application No. 63/338,794, filed on May 5, 2022, provisional application No. 63/338,806, filed on May 5, 2022, provisional application No. 63/338,817, filed on May 5, 2022.

(51) Int. Cl.

| | |
|---|---|
| ***A61B 5/145*** | (2006.01) |
| ***A61B 17/135*** | (2006.01) |
| ***A61N 1/02*** | (2006.01) |
| ***A61N 1/05*** | (2006.01) |
| ***A61N 1/372*** | (2006.01) |
| ***G16H 10/40*** | (2018.01) |
| ***G16H 20/17*** | (2018.01) |
| *A61B 17/00* | (2006.01) |

(52) U.S. Cl.

CPC .......... *A61B 17/1355* (2013.01); *A61N 1/025* (2013.01); *A61N 1/0507* (2013.01); *A61N 1/0551* (2013.01); *A61N 1/0556* (2013.01); *A61N 1/0558* (2013.01); *A61N 1/36007* (2013.01); *A61N 1/3606* (2013.01); *A61N 1/36132* (2013.01); *A61N 1/36135* (2013.01); *A61N 1/36139* (2013.01); *A61N 1/36146* (2013.01); *A61N 1/36171* (2013.01); *A61N 1/36185* (2013.01); *A61N 1/37247* (2013.01); *G16H 10/40* (2018.01); *G16H 20/17* (2018.01); *A61B 2017/00867* (2013.01); *A61N 1/3605* (2013.01)

(58) Field of Classification Search

CPC .............. A61N 1/0558; A61N 1/36007; A61N 1/3606; A61N 1/36135; A61N 1/36139; A61N 1/36146; A61N 1/36171; A61N 1/36185; A61N 1/37247; A61N 1/3605; A61B 5/14532; A61B 5/7435; A61B 5/0022; A61B 5/4836; A61B 5/01; A61B 5/02438; A61B 5/053; A61B 5/1123; A61B 5/14551; A61B 5/392; A61B 5/1118; A61B 5/686; A61B 17/1355; A61B 2562/2019; A61B 7/008; G16H 10/40; G16H 20/17; G16H 20/30; G16H 50/20; G16H 50/70; G16H 40/67; G16H 40/63

See application file for complete search history.

(56) References Cited

U.S. PATENT DOCUMENTS

| | | | | |
|---|---|---|---|---|
| 5,487,756 | A | 1/1996 | Kallesoe et al. | |
| 6,572,543 | B1 | 6/2003 | Christopherson et al. | |
| 7,069,078 | B2 | 6/2006 | Houben | |
| 7,369,897 | B2 | 5/2008 | Boveja et al. | |
| 7,702,386 | B2 | 4/2010 | Dobak et al. | |
| 7,818,069 | B2 | 10/2010 | Colborn et al. | |
| 8,244,347 | B2 | 8/2012 | Lozano | |
| 8,340,760 | B2 | 12/2012 | Dobak, III | |
| 8,428,719 | B2 | 4/2013 | Napadow | |
| 8,868,211 | B2 | 10/2014 | Durand et al. | |
| 9,033,969 | B2 | 5/2015 | Azamian et al. | |
| 9,833,621 | B2 | 12/2017 | Levine | |
| 9,937,344 | B2 * | 4/2018 | Starkebaum ....... | A61N 1/36007 |
| 9,974,955 | B2 | 5/2018 | Thornton et al. | |
| 10,292,596 | B2 | 5/2019 | Shadforth et al. | |
| 10,750,994 | B2 | 8/2020 | Annoni et al. | |
| 10,850,100 | B2 | 12/2020 | Cakmak | |
| 10,856,926 | B2 | 12/2020 | Azamian et al. | |
| 11,191,966 | B2 | 12/2021 | Wah | |
| 2006/0282145 | A1 | 12/2006 | Caparso et al. | |
| 2007/0027484 | A1 | 2/2007 | Guzman et al. | |
| 2008/0039904 | A1 | 2/2008 | Bulkes et al. | |
| 2008/0046055 | A1 | 2/2008 | Durand et al. | |
| 2008/0154177 | A1 | 6/2008 | Moubayed et al. | |
| 2008/0215101 | A1 | 9/2008 | Rezai et al. | |
| 2008/0234780 | A1 | 9/2008 | Smith et al. | |
| 2009/0254143 | A1 | 10/2009 | Tweden et al. | |
| 2010/0210955 | A1 | 8/2010 | Forsell | |
| 2011/0147046 | A1 | 6/2011 | Bonde et al. | |
| 2011/0172732 | A1 | 7/2011 | Maschino | |
| 2011/0264116 | A1 | 10/2011 | Kocur et al. | |
| 2011/0301408 | A1 | 12/2011 | Augarten | |
| 2013/0165994 | A1 | 6/2013 | Ternes et al. | |
| 2014/0074188 | A1 | 3/2014 | Armstrong et al. | |
| 2014/0228900 | A1 | 8/2014 | Osorio | |
| 2015/0045850 | A1 | 2/2015 | Bork et al. | |
| 2015/0148869 | A1 | 5/2015 | Dorvall et al. | |
| 2015/0328464 | A1 | 11/2015 | Henry et al. | |
| 2015/0374296 | A1 | 12/2015 | Baru et al. | |
| 2016/0114165 | A1 | 4/2016 | Levine et al. | |
| 2017/0021174 | A1 * | 1/2017 | Thornton ........... | A61N 1/36007 |
| 2017/0164876 | A1 | 6/2017 | Hyde et al. | |
| 2018/0085580 | A1 * | 3/2018 | Perez .................. | A61N 1/0456 |
| 2018/0104500 | A1 | 4/2018 | Blum | |
| 2018/0125689 | A1 | 5/2018 | Perez et al. | |
| 2018/0303648 | A1 | 10/2018 | Mische | |
| 2018/0326162 | A1 | 11/2018 | Bral | |
| 2019/0125226 | A1 | 5/2019 | Koya | |
| 2019/0125227 | A1 | 5/2019 | Koya et al. | |
| 2019/0174891 | A1 | 6/2019 | Nieves | |
| 2019/0175915 | A1 | 6/2019 | Brill et al. | |
| 2019/0192851 | A1 | 6/2019 | Possover | |
| 2019/0216384 | A1 | 7/2019 | Duval et al. | |
| 2019/0329040 | A1 | 10/2019 | Mustakos et al. | |
| 2019/0339224 | A1 | 11/2019 | Bhavaraju et al. | |
| 2020/0206496 | A1 | 7/2020 | Meng | |
| 2020/0230400 | A1 | 7/2020 | Shepard et al. | |
| 2020/0230412 | A1 | 7/2020 | Rondoini et al. | |
| 2020/0254259 | A1 | 8/2020 | Libbus et al. | |
| 2021/0146136 | A1 | 5/2021 | Waataja et al. | |
| 2021/0244949 | A1 | 8/2021 | Soin | |
| 2021/0275819 | A1 | 9/2021 | Boor et al. | |
| 2021/0290949 | A1 | 9/2021 | Holinski | |
| 2022/0062621 | A1 | 3/2022 | Hogg | |

(56) References Cited

U.S. PATENT DOCUMENTS

| | | | |
|---|---|---|---|
| 2022/0193414 A1 | 6/2022 | Waataja et al. |
| 2023/0000447 A1 | 1/2023 | Mikhno |

FOREIGN PATENT DOCUMENTS

| | | |
|---|---|---|
| WO | WO 2020/214982 | 10/2020 |
| WO | WO 2020/252428 | 12/2020 |
| WO | WO 2020/254795 | 12/2020 |
| WO | WO 2021/119741 | 6/2021 |

OTHER PUBLICATIONS

Bergner et al. "Diabetes mellitus and sudden cardiac death," Cardiology Journal, 2010, vol. 17, No. 2, pp. 117-129.
Chow et al. "Risk of Cardiac Arrhythmias During Hypoglycemia in Patients with Type 2 Diabetes and Cardiovascular Risk," Diabetes, May 2014, vol. 63, No. 5, pp. 1738-1747.
Hanefeld et al. "Hypoglycemia and Cardiovascular Risk: Is There a Major Link?" Diabetes Care, 2016, vol. 39, Suppl. 2, pp. S205-S209.
Hirotani et al. "Carbon Nanotube Thin Films for High-Performance Flexible Electronics Applications," Topics in Current Chemistry, Jan. 2019, vol. 377, No. 1, Article No. 3.
Hsieh et al. "The enigma of the dead-in-bed syndrome: challenges in predicting and preventing this devastating complication of type 1 diabetes," Journal of Diabetes and its Complications, 2014, vol. 28, pp. 585-587.
Jones et al. "Neuromodulation using ultra low frequency current waveform reversibly blocks axonal conduction and chronic pain," Science Translational Medicine, Aug. 2021, vol. 13, No. 608, article eabg9890.
Jovanov et al. "Sensors and Systems for Obesity Care and Research," IEEE, 36th Annual International Conference of the IEEE Engineering in Medicine and Biology Society, Aug. 2014, pp. 3188-3191.
Murastov et al. "Flexible and water-stable graphene-based electrodes for long-term use in bioelectronics," Biosensors and Bioelectronics, Oct. 2020, vol. 166, Article 112426.
Shapiro et al. Pudendal Nerve Block by Low-Frequency (≤1 kHz) Biphasic Electrical Stimulation, Neuromodulations, Aug. 2021, vol. 24, No. 6, pp. 1012-1017.
Tancredi et al. "Excess Mortality among Persons with Type 2 Diabetes," The New England Journal of Medicine, 2015, vol. 373, pp. 1720-1732.
Yi et al. "The role of the autonomic nervous liver innervation in the control of energy metabolism," Biochimica et Biophysica Acta, Apr. 2010, vol. 1802, No. 4, pp. 416-431.
Zaccardi et al. "Diabetes mellitus and risk of sudden cardiac death," International Journal of Cardiology, Dec. 2014, vol. 177, No. 2, pp. 535-537.
International Search Report and Written Opinion for International (PCT) Patent Application No. PCT/US2023/065510, dated Jul. 11, 2023 10 pages.
International Search Report and Written Opinion for International (PCT) Patent Application No. PCT/US2023/065428, dated Jul. 20, 2023 12 pages.
International Preliminary Report on Patentability for International (PCT) Patent Application No. PCT/US2023/065510, dated Nov. 14, 2024 7 pages.
International Preliminary Report on Patentability for International (PCT) Patent Application No. PCT/US2023/065428, dated Nov. 14, 2024 8 pages.
Official Action for U.S. Appl. No. 18/131,500, dated May 21, 2025 6 pages Restriction Requirement.
Official Action for U.S. Appl. No. 18/131,500, dated Jul. 28, 2025 10 pages.
Official Action for U.S. Appl. No. 18/131,513, dated Jun. 4, 2025 12 pages.
Official Action for U.S. Appl. No. 18/131,542, dated Jul. 3, 2025 21 pages.
Official Action for U.S. Appl. No. 18/131,576, dated Jun. 20, 2025 22 pages.
Official Action for U.S. Appl. No. 18/131,576, dated Oct. 7, 2025 20 pages.
Official Action for U.S. Appl. No. 18/131,592, dated Jun. 11, 2025 15 pages.
Official Action for U.S. Appl. No. 18/131,592, dated Sep. 19, 2025 19 pages.
Official Action for U.S. Appl. No. 18/132,186, dated Aug. 19, 2025 24 pages.
Official Action for U.S. Appl. No. 18/131,614, dated Sep. 17, 2025 8 pages.
Official Action for U.S. Appl. No. 18/132,219, dated Jun. 30, 2025 16 pages.
Official Action for U.S. Appl. No. 18/132,232, dated Jul. 17, 2025 20 pages.
Official Action for European Patent Application No. 23721235.2, dated Oct. 23, 2025, 4 pages.
Official Action for U.S. Appl. No. 18/131,500, dated Jan. 8, 2026 11 pages.
Official Action for U.S. Appl. No. 18/131,513, dated Dec. 10, 2025 11 pages.
Official Action for U.S. Appl. No. 18/131,542, dated Oct. 24, 2025 24 pages.
Official Action for U.S. Appl. No. 18/131,614, dated Nov. 10, 2025 29 pages.
Notice of Allowance for U.S. Appl. No. 18/132,219, dated Nov. 13, 2025 11 pages.
Official Action for U.S. Appl. No. 18/132,232, dated Nov. 21, 2025 28 pages.
Notice of Allowance for U.S. Appl. No. 18/131,513, dated Apr. 3, 2026 8 pages.
Official Action for U.S. Appl. No. 18/131,542, dated Mar. 10, 2026 25 pages.
Notice of Allowance for U.S. Appl. No. 18/131,576, dated Mar. 11, 2026 8 pages.
Official Action for U.S. Appl. No. 18/862,817, dated Jun. 3, 2026 43 pages.
Official Action for U.S. Appl. No. 18/132,186, dated Mar. 4, 2026 26 pages.
Official Action for U.S. Appl. No. 18/131,614, dated Apr. 9, 2026 11 pages.
Notice of Allowance for U.S. Appl. No. 18/132,204, dated Mar. 20, 2026 9 pages.
Notice of Allowance for U.S. Appl. No. 18/132,204, dated Jun. 10, 2026 10 pages.
Notice of Allowance for U.S. Appl. No. 18/131,542, dated Jul. 2, 2026 8 pages.
Notice of Allowance for U.S. Appl. No. 18/131,576, dated Jul. 1, 2026 8 pages.
Official Action for U.S. Appl. No. 18/862,801, dated Jul. 13, 2026 10 pages.
Official Action for U.S. Appl. No. 18/132,186, dated Jul. 22, 2026 28 pages.

* cited by examiner

NEUROMODULATION TECHNIQUES TO CREATE A NERVE BLOCKAGE WITH A COMBINATION STIMULATION/BLOCK THERAPY FOR GLYCEMIC CONTROL

CROSS REFERENCE TO RELATED APPLICATIONS

This application claims the benefit of U.S. Provisional Application No. 63/339,101, filed on May 6, 2022, entitled "Neuromodulation Techniques to Create a Nerve Blockage with a Combination Stimulation/Block Therapy for Glycemic Control"; U.S. Provisional Application No. 63/338,794, filed on May 5, 2022, entitled "Systems and Methods for Stimulating an Anatomical Element Using an Electrode Device"; U.S. Provisional Application No. 63/339,049, filed on May 6, 2022, entitled "Systems and Methods for Mechanically Blocking a Nerve"; U.S. Provisional Application No. 63/338,806, filed on May 5, 2022, entitled "Systems and Methods for Wirelessly Stimulating or Blocking at Least One Nerve"; U.S. Provisional Application No. 63/339,136, filed on May 6, 2022, entitled "Neuromodulation for Treatment of Neonatal Chronic Hyperinsulinism"; U.S. Provisional Application No. 63/342,945, filed on May 17, 2022, entitled "Neuromodulation Techniques for Treatment of Hypoglycemia"; U.S. Provisional Application No. 63/342,998, filed on May 17, 2022, entitled "Closed-Loop Feedback and Treatment"; U.S. Provisional Application No. 63/338,817, filed on May 5, 2022, entitled "Systems and Methods for Monitoring and Controlling an Implantable Pulse Generator"; U.S. Provisional Application No. 63/339,024, filed on May 6, 2022, entitled "Programming and Calibration of Closed-Loop Vagal Nerve Stimulation Device"; U.S. Provisional Application No. 63/339,304, filed on May 6, 2022, entitled "Systems and Methods for Stimulating or Blocking a Nerve Using an Electrode Device with a Sutureless Closure"; U.S. Provisional Application No. 63/339,154, filed on May 6, 2022, entitled "Personalized Machine Learning Algorithm for Stimulation/Block Therapy for Treatment of Type 2 Diabetes"; U.S. Provisional Application No. 63/342,967, filed on May 17, 2022, entitled "Patient User Interface for a Stimulation/Block Therapy for Treatment of Type 2 Diabetes"; and U.S. Provisional Application No. 63/339,160, filed on May 6, 2022, entitled "Utilization of Growth Curves for Optimization of Type 2 Diabetes Treatment", all of which applications are incorporated herein by reference in their entireties.

BACKGROUND

The present disclosure is generally directed to therapeutic neuromodulation and relates more particularly to a stimulation/block therapy to affect glycemic control of a patient.

Diabetes represents a large and growing global health issue with estimates of over 537 million patients worldwide having been diagnosed with type 2 diabetes and estimates of 6.7 million annual deaths related to complications of diabetes. Despite different types of treatments being developed and utilized (e.g., medication, surgery, diet, etc.), type 2 diabetes remains challenging to effectively treat. Type 2 patients must frequently contend with keeping their blood sugar levels in a desirable glycemic range. Prolonged deviations can lead to long term complications such as retinopathy, nephropathy (e.g., kidney damage), cardiovascular disease, etc. Because treatment for diabetes is self-managed by the patient on a day-to-day basis (e.g., the patients self-inject the insulin), compliance or adherence with treatments can be problematic.

BRIEF SUMMARY

Example aspects of the present disclosure include:

A system for stimulating an anatomical element of a patient, comprising: an implantable pulse generator configured to generate a current; an electrode device electrically coupled to the implantable pulse generator, the electrode device comprising a plurality of electrodes configured for placement on or around the anatomical element of the patient; a processor; and a memory storing data for processing by the processor, the data, when processed, causes the processor to: transmit instructions to the implantable pulse generator to apply the current generated to the anatomical element of the patient via the plurality of electrodes of the electrode device, wherein the current is applied using a first waveform of a plurality of waveforms that the implantable pulse generator is capable of generating, each of the plurality of waveforms comprising a substantially similar charge density.

Any of the aspects herein, wherein the anatomical element comprises a celiac vagal trunk and a hepatic vagal trunk of the patient.

Any of the aspects herein, wherein the first waveform comprises a frequency between 0.1 and 20 hertz (Hz).

Any of the aspects herein, wherein the first waveform comprises a biphasic pulse.

Any of the aspects herein, wherein the first waveform comprises a square wave shape, a trapezoidal wave shape, a sinusoidal wave shape, or another wave shape that is charge balanced.

Any of the aspects herein, wherein the memory stores further data for processing by the processor that, when processed, causes the processor to: transmit instructions to the implantable pulse generator to increase a frequency, an amplitude, or both of the first waveform incrementally when applying the current.

Any of the aspects herein, wherein the frequency, the amplitude, or both of the first waveform are incrementally increased over time to generate a desired shape for the first waveform.

Any of the aspects herein, wherein the data stored in the memory that, when processed causes the processor to transmit instructions to the implantable pulse generator to apply the current using the first waveform further causes the system to: transmit instructions to the implantable pulse generator to apply a pattern of stimulation pulses to the anatomical element to simulate a physiological neuron spiking behavior at the anatomical element, wherein the first waveform comprises the pattern of stimulation pulses.

Any of the aspects herein, wherein the first waveform comprises a standard shape that is determined based at least in part on a plurality of patient studies, common physiological patterns, or a combination thereof.

Any of the aspects herein, wherein the first waveform comprises a shape that is determined based at least in part on observing signaling on the anatomical element at different stages of a metabolic cycle of the patient.

Any of the aspects herein, wherein the pattern of stimulation pulses is regular or non-regular.

Any of the aspects herein, wherein the memory stores further data for processing by the processor that, when processed, causes the processor to: manipulate a circadian cycle associated with the anatomical element based at least in part on indicating for the implantable pulse generator to apply the current using the first waveform.

Any of the aspects herein, wherein the first waveform modulates a first tone of the anatomical element to match a second tone of the anatomical element, the second tone representative of time periods of minimal activity of the patient.

A system for providing a pharmacological blockade at an anatomical element of a patient, comprising: a micropump configured to deliver a pharmacological agent to the anatomical element; a processor; and a memory storing data for processing by the processor, the data, when processed, causes the processor to: transmit instructions to the micropump to deliver the pharmacological agent to the anatomical element via the micropump, wherein the pharmacological agent blocks a physiological response of the anatomical element, the physiological response of the anatomical element comprising an increase in glucose production in the patient.

Any of the aspects herein, wherein the anatomical element comprises a hepatic vagal trunk of the patient.

Any of the aspects herein, wherein the anatomical element comprises a liver of the patient, receptors on a surface of the liver, or a combination thereof.

Any of the aspects herein, wherein the pharmacological agent blocks the liver from producing glucose and stimulates neural pathways of the patient to release glucagon.

Any of the aspects herein, wherein the pharmacological agent mimics actions of an insulin hormone or glucagon hormone.

A system for stimulating an anatomical element of a patient, comprising: an implantable pulse generator configured to generate a current; an electrode device comprising: a body; and a plurality of electrodes disposed on the body and configured to apply the current to the anatomical element; a processor; and a memory storing data for processing by the processor, the data, when processed, causes the processor to: transmit instructions to the implantable pulse generator to apply the current generated to the anatomical element of the patient via the plurality of electrodes of the electrode device, wherein the current is applied using a first waveform of a plurality of waveforms that the implantable pulse generator is capable of generating, each of the plurality of waveforms comprising a substantially similar charge density.

Any of the aspects herein, wherein the anatomical element comprises a celiac vagal trunk and a hepatic vagal trunk of the patient.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
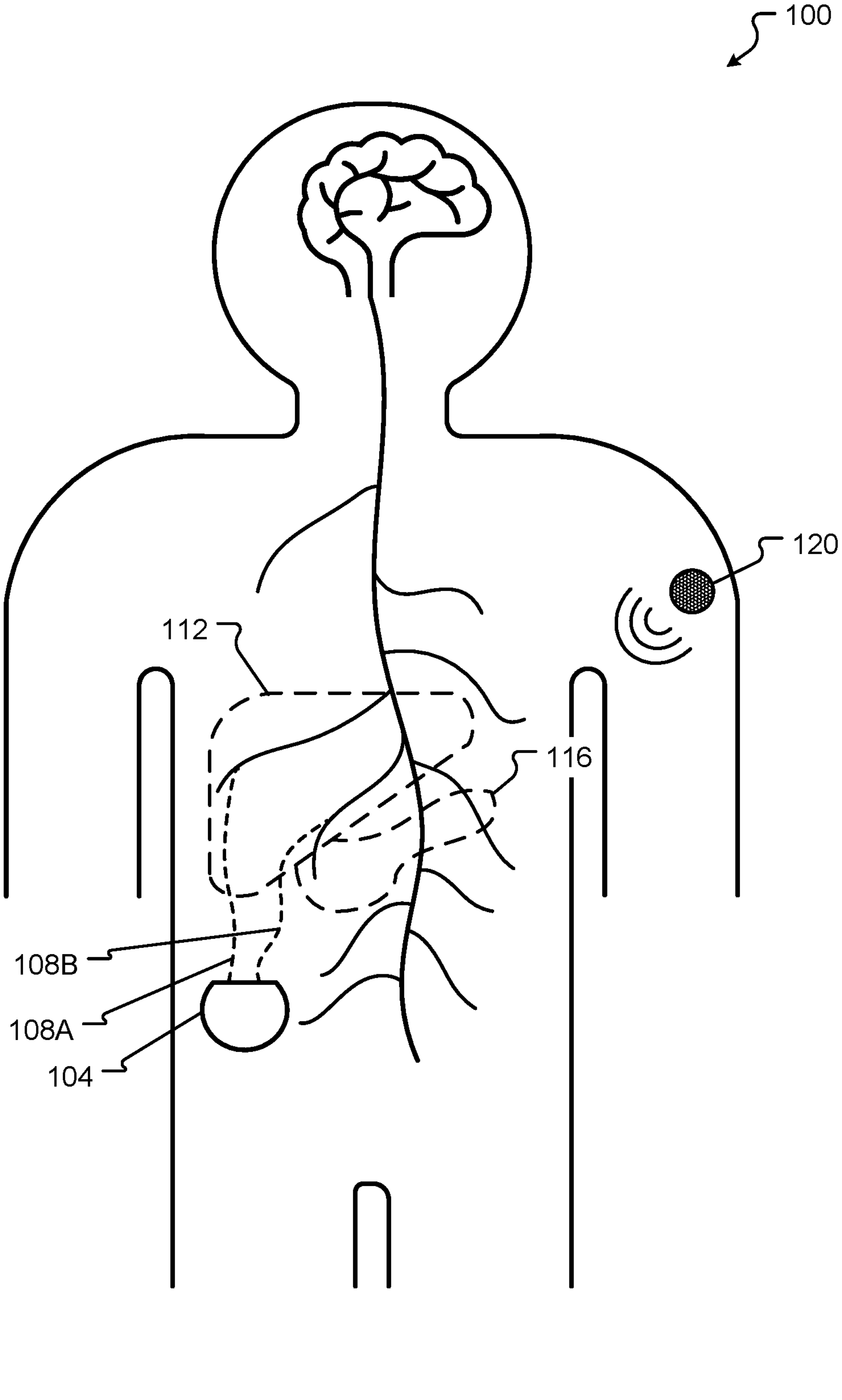
FIG. 1 is a diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., random-access memory (RAM), read-only memory (ROM), electrically erasable programmable ROM (EEPROM), flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10× Fusion processors; Apple A11, A12, A12X, A12Z, or A13 Bionic processors; or any other general purpose microprocessors), graphics processing units (e.g., Nvidia Geforce RTX 2000-series processors, Nvidia Geforce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements. The processors listed herein are not intended to be an exhaustive list of all possible processors that can be used for implementation of the described techniques, and any future iterations of such chips, technologies, or processors may be used to implement the techniques and embodiments of the present disclosure as described herein.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Vagus nerve stimulation (VNS) is a technology that has been developed to treat different disorders or ailments of a patient, such as epilepsy and depression. In some examples, VNS involves placing a device in or on a patient's body that uses electrical impulses to stimulate the vagus nerve. For example, the device may be usually placed under the skin of the patient, where a wire (e.g., lead) and/or electrode connects the device to the vagus nerve. Once the device is activated, the device sends signals through the vagus nerve to the patient's brainstem (e.g., or different target area in the patient, such as other organs of the patient), transmitting information to their brain. For example, with VNS, the device may be configured to send regular, mild pulses of electrical energy to the brain via the vagus nerve. In some examples, the device may be referred to as an implantable pulse generator. An implantable vagus nerve stimulator has been approved to treat epilepsy and depression in qualifying patients.

The vagus nerve (e.g., also called the pneumogastric nerve, vagal nerve, the cranial nerve X, etc.) is responsible for various internal organ functions of a patient, including digestion, heart rate, breathing, cardiovascular activity, and reflex actions (e.g., coughing, sneezing, swallowing, and vomiting). Most patients may have one vagus nerve on each side of their body, with numerous branches running from their brainstem through their neck, chest, and abdomen down to part of their colon. The vagus nerve plays a role in many bodily functions and may form a link between different areas of the patient, such as the brain and the gut. The vagus nerve is a critical nerve for supplying parasympathetic information to the visceral organs of the respiratory, digestive, and urinary systems. Additionally, the vagus nerve is important in the control of heart rate, bronchoconstriction, and digestive processes. In some cases, the vagus nerve may be considered a mixed nerve based on including both afferent (sensory) fibers and efferent (motor) fibers. As such, based on including the two types of fibers, the vagus nerve may be responsible for carrying motor signals to organs for innervating the organs (e.g., via the efferent fibers), as well as carrying sensory information from the organs back to the brain (e.g., via the afferent fibers).

The vagus nerve has a number of different functions. Four key functions of the vagus nerve are carrying sensory signals, carrying special sensory signals, providing motor functions, and assisting in parasympathetic functions. For example, the sensory signals carried by the vagus nerve may include signaling between the brain and the throat, heart, lungs, and abdomen. The special sensory signals carried by the vagus nerve may provide signaling of special senses in the patient, such as the taste sensation behind the tongue. Additionally, the vagus nerve may enable certain motor functions of the patient, such as providing movement functions for muscles in the neck responsible for swallowing and speech. The parasympathetic functions provided by the vagus nerve may include digestive tract, respiration, and heart rate functioning. In some cases, the nervous system can be divided into two areas: sympathetic and parasympathetic. The sympathetic side increases alertness, energy, blood pressure, heart rate, and breathing rate. The parasympathetic side, which the vagus nerve is heavily involved in, decreases alertness, blood pressure, and heart rate, and helps with calmness, relaxation, and digestion.

VNS is considered a type of neuromodulation (e.g., a technology that acts directly upon nerves of a patient, such as the alteration, or "modulation," of nerve activity by delivering electrical impulses or pharmaceutical agents directly to a target area). For example, as described above, VNS may include using a device (e.g., implanted in a patient or attached to the patient) that is configured to send regular, mild pulses of electrical energy to a target area of the patient (e.g., brainstem, organ, etc.) via the vagus nerve. The electrical pulses or impulses may affect how that target area of the patient functions to potentially treat different disorders or ailments of a patient.

In some examples, for epileptic patients that suffer from seizures, VNS may change how brain cells work by applying electrical stimulation to certain areas involved in seizures. For example, research has shown that VNS may help control seizures by increasing blood flow in key areas, raising levels of some brain substances (e.g., neurotransmitters) important to control seizures, changing electroencephalogram (EEG) patterns during a seizure, etc. As an example, an epileptic patient's heart rate may increase during a seizure or epileptic episode, so the VNS device may be programmed to send stimulation to the vagus nerve regular intervals and when periods of increased heart rate are seen, where applying stimulation at those times of increased heart rate may help stop seizures. Additionally or alternatively, depression has been tied to an imbalance in certain brain chemicals (e.g., neurotransmitters), so VNS is believed to assist in treating patients diagnosed with depression by using electricity (e.g., electrical pulses/impulses) to influence the production of those brain chemicals.

Diabetes represents a large and growing global health issue with estimates of over 537 million patients worldwide having been diagnosed with type 2 diabetes and estimates of 6.7 million annual deaths related to complications of diabetes. Despite different types of treatments being developed and utilized (e.g., medication, surgery, diet, etc.), type 2 diabetes remains challenging to effectively treat. Type 2 patients must frequently contend with keeping their blood sugar levels in a desirable glycemic range. Prolonged deviations can lead to long term complications such as retinopathy, nephropathy (e.g., kidney damage), cardiovascular disease, etc. Because treatment for diabetes is self-managed by the patient on a day-to-day basis (e.g., the patients self-inject the insulin), compliance or adherence with treatments can be problematic. Additionally, in a financial sense, global expenditures for type 2 diabetes treatments, preventive measures, and resulting consequences are estimated at about $966 billion per year. Compounding this issue of high global expenditures is the increasing price of insulin.

As described herein, a neuromodulation technique is provided for glycemic control (e.g., as a treatment for diabetes) using a stimulation/block therapy (e.g., type of VNS). For example, the neuromodulation technique may generally include using a device (e.g., including at least an implantable pulse generator) to provide electrical stimulation (e.g., electrical pulses/impulses) on one or more trunks of the vagus nerve (e.g., vagal trunks) to mute a glycemic response for patients with diabetes. The "patient" as used herein may refer to *Homo sapiens* or any other living being that has a vagus nerve.

In some examples, the device may provide stimulation/blocking of the celiac and hepatic vagal trunks (e.g., using the device) for the purposes of glycemic control. For example, the anterior sub diaphragmatic vagal trunk at the hepatic branching point of the vagus nerve may be electrically blocked (e.g., down-regulated) by delivering a high frequency stimulation (e.g., of about 5 kilohertz (kHz) or in a range between 1 kHz to 50 kHz). Additionally or alternatively, the posterior sub diaphragmatic vagal trunk at the celiac branching point of the vagus nerve may be electrically stimulated (e.g., up-regulated) by delivering a low frequency stimulation (e.g., a square wave at 1 Hz or within a range from 0.1 Hz to 20 Hz). In some examples, the electrical blocking and/or electrical stimulating of the respective vagal trunks may be performed by using one or more cuff electrodes (e.g., of the device) placed on the corresponding vagal trunks (e.g., sutured or otherwise held in place). The desired response by providing the stimulation/block therapy is a muting of the glycemic response of a patient. In some examples, muting of the glycemic response may refer to a lower post prandial peak of the glycemic response as compared to a peak without the stimulation/block therapy being applied.

Using the stimulation/block therapy to achieve a muting of the glycemic response is advantageous for those with type 2 diabetes where the postprandial glycemic response (e.g., occurring after a meal) can be very high. For example, some patients with type 2 diabetes may have high blood sugar levels (e.g., glucose levels) after eating a meal based on their reduced or lack of insulin production (e.g., normal insulin production in the body lowers blood sugar levels postprandially by promoting absorption of glucose from the blood into different cells). Additionally or alternatively, patients diagnosed with type 2 diabetes may generally have high glycemic levels at different points of the day (e.g., not necessarily postprandially or immediately after a meal). Over time, the effect of high glycemic values can have a detrimental effect on one's health, leading to neuropathy, retinopathy, and other ailments. Accordingly, by using the stimulation/block therapy provided herein, a high glycemic response experienced by type 2 diabetes patients may be muted (e.g., the glycemic response is reduced, particularly post prandially). Additionally, the therapy aims to improve insulin sensitivity by blocking hepatic glucose production and also by stimulating pancreatic insulin production needed for glycemic control, where the lack of insulin sensitivity can potentially lead to an imbalance in glycemic control and consequent systemic complications in patients with type 2 diabetes. In some examples, the therapy may also improve fasting hyperglycemia, which can be commonly seen in patients with type 2 diabetes.

Rather than transmitting a pure electrical signaling to the vagus nerve to provide the stimulation/blocking therapy as described herein for supporting glycemic control in a patient, other options may be implemented to produce a same effect on a glycemic response of the patient. For example, the techniques described herein for providing the stimulation/blocking therapy to support glycemic control in the patient may use a low frequency parasympathetic vagal blockade. The low frequency parasympathetic vagal blockade may use a low frequency may span between 0.1 and 20 Hz in a biphasic pulse that provides selective blocking. Additionally, a waveform for the low frequency signal to provide the blocking may be different shapes (e.g., square, trapezoidal, or any such shape that is charge balanced). Additionally, a waveform for the low frequency signal can have varying pulse widths from 0.05 ms to 10 ms. The low frequency waveforms may be less energy intensive than higher frequency waveforms that can provide the blocking. The low frequency parasympathetic vagal blockade is described in greater detail with reference to FIGS. 2A-2D. In some examples, the low frequency waveforms may have a substantially similar or same charge density as each other, regardless of the specific frequency or specific waveform shape that is used to apply the stimulation/block therapy.

Additionally or alternatively, a waveform modulation may be used to support glycemic control in the patient. For example, the waveform modulation may include slowly increasing an amplitude and/or frequency of a pulse that provides the blocking to the vagus nerve (e.g., at the hepatic vagal trunk or the anterior sub diaphragmatic vagal trunk at the hepatic branching point of the vagus nerve), such that a desired shape for the pulse is achieved. Examples of waveform modulation techniques are described in greater detail with reference to FIG. 3. Additionally or alternatively, the techniques described herein may use a pharmacologic injection (e.g., via a micropump inserted in or located on the patient) to provide the blocking therapy. Pharmacologic blockade is a technique used to block pain in a patient. Subsequently, as described herein, a micropump (e.g., or other type of device) may be used to achieve a pharmacologic blockade via local delivery of an agent in the proximity of the sub diaphragmatic vagal trunk at the hepatic branching point (e.g., of the vagus nerve). Using a micropump to deliver a pharmacological agent locally to achieve a pharmacological blockade is described in greater detail with reference to FIG. 4.

In some examples, additional strategies, techniques, or options may be used to induce a block at the hepatic vagal trunk of the patient. For example, neural coding may be used to induce the block (e.g., "telling" the nerve to interrupt signaling). Neural coding may be achieved by a regular or nonregular pattern of stimulation pulses that simulate physiological neuron spiking behavior. The waveform(s) for regular or nonregular pattern of stimulation pulses may be standard (e.g., generalized from many patient studies or based on common physiological patterns) or may be learned by observing the signaling on the corresponding nerves at different points in metabolic cycling for the patient.

Additionally or alternatively, techniques for inducing the block may include manipulating a circadian cycle of the patient to downregulate the liver (e.g., "tricking" the liver to think it is night or that the patient is sleeping). Stimulation waveforms may be used to signal the liver into entering a quiescent state (e.g., a state or period of inactivity or dormancy) by modulation of a nervous system tone (e.g., a tone is an internal biological process that represents the activity of a given nerve, such as a vagal tone for the vagus nerve) to match a tone representative of less active periods (e.g., such as sleep). Additionally or alternatively, techniques for inducing the block may include delivering glucose to the liver. For example, the techniques to induce the block may include delivering glucose to sensing elements of the liver in a microenvironment or by delivering glucose to receptors on the liver surface to circumvent a systemic response. Accordingly, delivering glucose to the liver may block the liver from adding more glucose but also causes other neural pathways to release glucagon (e.g., causes the liver to "believe" it is in a high energy environment).

Embodiments of the present disclosure provide technical solutions to one or more of the problems of (1) high energy intensive stimulation therapies and (2) pure electrical stimulation therapies. For example, using low frequency stimulation with different waveform shapes to achieve a vagal blockade may be less energy intensive than using higher frequencies to electrically block signals on a nerve (e.g., vagus nerve). Additionally or alternatively, using a micropump to locally deliver pharmacological agent(s) to parts of the body may preempt the need of providing electrical stimulations to nerves in the body, thereby reducing potential difficulties of inserting and attaching necessary elements needed to provide the electrical stimulations (e.g., implantable pulse generator, electrodes, etc.).

Turning to FIG. 1, a diagram of a system 100 according to at least one embodiment of the present disclosure is shown. The system 100 may be used to provide glycemic control for a patient and/or carry out one or more other aspects of one or more of the methods disclosed herein. For example, the system 100 may include at least a device 104 that is capable of providing a stimulation/blocking therapy that mutes a glycemic response for patients with diabetes. In some examples, the device 104 may be referred to as an implantable pulse generator, an implantable neurostimulator, or another type of device not explicitly listed or described herein. Additionally, the system 100 may include one or more wires 108 (e.g., leads) that provide a connection between the device 104 and nerves of the patient for enabling the stimulation/blocking therapy.

As described previously, neuromodulation techniques (e.g., technologies that act directly upon nerves of a patient, such as the alteration, or "modulation," of nerve activity by delivering electrical impulses or localized pharmaceutical agents directly to a target area) may be used for assisting in treatments for different diseases, disorders, or ailments of a patient, such as epilepsy and depression. Accordingly, as described herein, the neuromodulation techniques may be used for muting a glycemic response in the patient to assist in the treatment of diabetes for the patient. For example, the device 104 may provide electrical stimulation to one or more trunks of the vagus nerve of the patient (e.g., via the one or more wires 108) to provide the stimulation/blocking therapy for supporting glycemic control in the patient.

In some examples, the one or more wires 108 may include at least a first wire 108A and a second wire 108B connected to respective vagal trunks (e.g., different trunks of the vagus nerve). As described previously, most patients have one vagus nerve on each side of their body, running from their brainstem through their neck, chest, and abdomen down to part of their colon. The vagus nerve plays a role in many bodily functions and may form a link between different areas of the patient, such as the brain and the gut. For example, the vagus nerve is responsible for various internal organ functions of a patient, including digestion, heart rate, breathing, cardiovascular activity, and reflex actions (e.g., coughing, sneezing, swallowing, and vomiting).

Accordingly, the first wire 108A may be connected to a first vagal trunk of the patient (e.g., the anterior sub diaphragmatic vagal trunk at the hepatic branching point of the vagus nerve) to provide an electrical blocking signal (e.g., a down-regulating signal) from the device 104 to that first vagal trunk (e.g., by delivering a high frequency stimulation, such as a given waveform at about 5 kHz). Additionally or alternatively, the second wire 108B may be connected to a second vagal trunk of the patient (e.g., the posterior sub diaphragmatic vagal trunk at the celiac branching point of the vagus nerve) to provide an electrical stimulation signal (e.g., an up-regulating signal) from the device 104 to that second vagal trunk (e.g., by delivering a low frequency stimulation, such as a square wave or other waveform at 1 Hz). By providing the electrical blocking signal and the electrical stimulation signal to the respective vagal trunks, the system 100 may provide a muting of the glycemic response of the patient when the stimulation/blocking therapy is applied. For example, muting of the glycemic response may refer to a lower post prandial peak of the glycemic response as compared to a peak without the stimulation/block therapy being applied.

In some examples, the vagal trunks to which the wires 108 are connected may be connected to or otherwise in the vicinity of one or more organs of the patient, such that the blocking/stimulation signals provided to the respective vagal trunks by the wires 108 and the device 104 are delivered to the one or more organs. For example, the first vagal trunk (e.g., to which the first wire 108A is connected) may be connected to a first organ 112 of the patient, and the second vagal trunk (e.g., to which the second wire 108B is connected) may be connected to a second organ 116. Additionally or alternatively, while the respective vagal trunks are shown as being connected to the corresponding organs of the patient as described, the vagal trunks to which the wires 108 are connected may be connected to the other organ (e.g., the first vagal trunk is connected to the second organ 116 and the second vagal trunk is connected to the first organ 112) or may be connected to different organs of the patient. In some examples, the first organ 112 may represent a liver of the patient, and the second organ 116 may represent a pancreas of the patient. In such examples, the blocking/stimulation signals provided by the wires 108 and the device 104 may be delivered to the liver and/or pancreas of the patient to mute a glycemic response of the patient as described herein.

In some examples, the wires 108 may provide the electrical signals to the respective vagal trunks via electrodes of an electrode device (e.g., cuff electrodes) that are connected to the vagal trunks (e.g., sutured in place, wrapped around the nerves of the vagal trunks, etc.). In some examples, the wires 108 may be referenced as cuff electrodes or may otherwise include the cuff electrodes (e.g., at an end of the wires 108 not connected or plugged into the device 104). Additionally or alternatively, while shown as physical wires that provide the connection between the device 104 and the one or more vagal trunks, the cuff electrodes may provide the electrical blocking and/or stimulation signals to the one or more vagal trunks wirelessly (e.g., with or without the device 104).

Additionally, while not shown, the system 100 may include one or more processors (e.g., one or more DSPs, general purpose microprocessors, graphics processing units, ASICs, FPGAs, or other equivalent integrated or discrete logic circuitry) that are programmed to carry out one or more aspects of the present disclosure. In some examples, the one or more processors may include a memory or may be otherwise configured to perform the aspects of the present disclosure. For example, the one or more processors may provide instructions to the device 104, the cuff electrodes, or other components of the system 100 not explicitly shown or described with reference to FIG. 1 for providing the stimulation/blocking therapy to promote glycemic control in a patient as described herein. In some examples, the one or more processors may be part of the device 104 or part of a control unit for the system 100 (e.g., where the control unit is in communication with the device 104 and/or other components of the system 100).

In some examples, the system 100 may also optionally include a glucose sensor 120 that communicates (e.g., wirelessly) with other components of the system 100 (e.g., the device 104, the one or more processors, etc.) to achieve better glycemic control in the patient. For example, the glucose sensor 120 may continuously monitor glucose levels of the patient, such that if the glucose sensor 120 determines glucose levels are outside a normal or desired range for the patient (e.g., glucose levels are too high or too low in the patient), the glucose sensor 120 may communicate that glucose levels are outside the normal or desired range to the device 104 (e.g., via the one or more processors) to signal for the device 104 to apply the stimulation/blocking therapy described herein to adjust glucose levels in the patient (e.g., mute the glycemic response to lower glucose levels in the patient, block insulin production in the patient as a possible technique to raise glucose levels in the patient, etc.).

The system 100 or similar systems may be used, for example, to carry out one or more aspects of any of the methods 500, 600, and/or 700 described herein. The system 100 or similar systems may also be used for other purposes. It will be appreciated that the human body has many vagal nerves and the stimulation and/or blocking therapies described herein may be applied to one or more vagal nerves, which may reside at any location of a patient (e.g., lumbar, thoracic, etc.). Further, a sequence of stimulations and/or blocking therapies may be applied to different nerves. For example, a low frequency stimulation may be applied to a first nerve and a high frequency blockade may be applied to a second nerve.

In some examples, as described herein, rather than transmitting a pure electrical signaling to the vagus nerve to provide the stimulation/blocking therapy for supporting glycemic control in a patient, other options may be implemented to produce a same effect on a glycemic response of the patient. For example, the techniques described herein for providing the stimulation/blocking therapy to support glycemic control in the patient may include applying a current generated by the device 104 to the vagus nerve of the patient (e.g., an anatomical element of the patient) via the wires 108 and the corresponding cuff electrodes. The current applied to the vagus nerve may include a first waveform selected from a set of waveforms the device 104 is capable of generating, where each waveform of the set of waveforms has a same charge density. For example, each of the waveforms may have a same charge density no matter what frequency or waveform shape is used to apply the current to the vagus nerve (e.g., a higher amplitude signal may be applied with a lower frequency or a lower amplitude signal may be applied with a higher frequency to achieve the same charge density).

The techniques described herein for providing the stimulation/blocking therapy to support glycemic control in the patient may use a low frequency parasympathetic vagal blockade. The low frequency parasympathetic vagal blockade may use a low frequency may span between 0.1 Hz and 20 Hz (e.g., in some examples, more specifically between 0.1 Hz and 0.9 Hz) in a biphasic pulse that provides selective blocking. Additionally, a waveform for the low frequency signal to provide the blocking may be different shapes (e.g., square, trapezoidal, or any such shape that is charge balanced). The low frequency waveforms may be less energy intensive than higher frequency waveforms that can provide the blocking. The low frequency parasympathetic vagal blockade is described in greater detail with reference to FIGS. 2A-2D. Accordingly, the low frequency waveforms may be applied to the first vagal trunk of the patient (e.g., the anterior sub diaphragmatic vagal trunk at the hepatic branching point of the vagus nerve) to provide an electrical blocking signal (e.g., a down-regulating signal) from the device 104 to that first vagal trunk rather than delivering a high frequency stimulation, such as a given waveform with a frequency between 1 kHz and 50 kHz (e.g., more specifically at about 5 kHz) to induce the block.

In some examples, additional strategies, techniques, or options may be used to induce a block at the hepatic vagal trunk of the patient. For example, neural coding may be used to induce the block (e.g., "telling" the nerve to interrupt signaling). Neural coding may be achieved by a regular or nonregular pattern of stimulation pulses that can simulate physiological neuron spiking behavior. That is, a pattern of stimulation pulses may be applied to the vagus nerve (e.g., anatomical element) to simulate a spiking behavior on the vagus nerve that results in the vagus nerve "telling" the brain of the patient to stop producing excess glucose. The waveform(s) for the regular or nonregular pattern of stimulation pulses may be standard (e.g., generalized from many patient studies or based on common physiological patterns) or may be learned by observing the signaling on the nerves at different points in metabolic cycling for the patient.

Additionally or alternatively, the techniques for inducing the block may include manipulating a circadian cycle of the patient to downregulate the liver (e.g., "tricking" the liver to think it is night or that the patient is sleeping). Stimulation waveforms (e.g., generated by the device 104) may be used to signal the liver into entering a quiescent state (e.g., a state or period of inactivity or dormancy) by modulation of a nervous system tone (e.g., a tone is an internal biological process that represents the activity of a given nerve, such as a vagal tone for the vagus nerve) to match a tone representative of less active periods (e.g., such as sleep). The stimulation waveforms may be applied directly to the liver or may be applied to the vagus nerve that carries the signal to the brain/liver.

The system 100 or similar systems may be used, for example, to carry out one or more aspects of any of the methods 500, 600, and/or 700 described herein. The system 100 or similar systems may also be used for other purposes.

FIGS. 2A-2D depict different waveform shapes that can be used for neuromodulation techniques to create a nerve blockage with a combination stimulation/block therapy for glycemic control as described herein. For example, as described previously, rather than transmitting a pure electrical signaling to an anatomical element (e.g., the vagus nerve) to provide a stimulation/blocking therapy for supporting glycemic control in a patient, other options may be implemented to produce a similar effect on a glycemic response of the patient. One example of another option to implement a glycemic response includes using a low frequency parasympathetic vagal blockade. With the low frequency parasympathetic vagal blockade, a low frequency signal may be used that spans between 0.1 and 20 Hz (e.g., between 0.1 and 0.9 Hz) in a biphasic pulse that provides selective blocking.

An electrode device comprising a plurality of electrodes may be configured to apply a current using the low frequency (generated by, for example, the device 104, such as an implantable pulse generator as described with reference to FIG. 1) to an anatomical element of a patient. It will be appreciated that in some embodiments, the electrode device may only comprise one electrode. The anatomical element may be, for example, one or more nerves and more specifically, a celiac vagal trunk and a hepatic vagal trunk. The electrode device may also comprise a body, and the plurality of electrodes may be coupled to, disposed on, or otherwise positioned on the body such that the plurality of electrodes is in contact with the anatomical element. The body may be designed so as to optimize current density and provide the current (e.g., stimulation and/or blocking) at different angles.

Figure 2A:
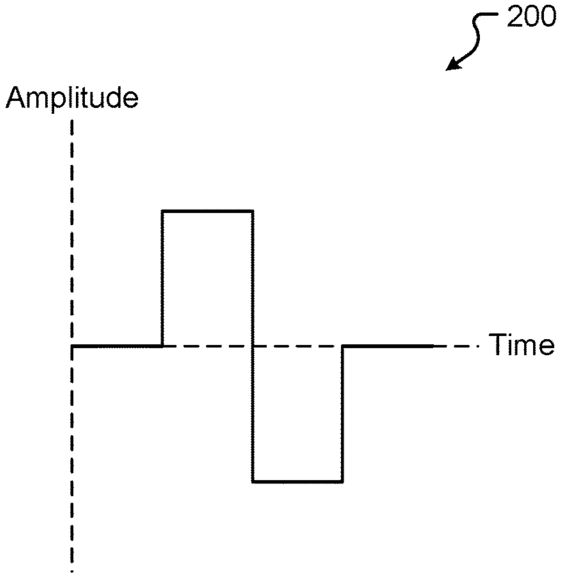
FIGS. 2A-2D are example waveform shapes that can be used that can be used for neuromodulation techniques according to at least one embodiment of the present disclosure.
Figure 2B:
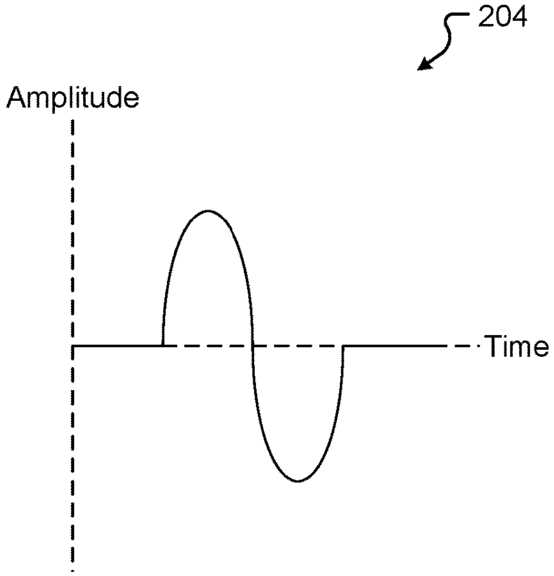
Figure 2C:
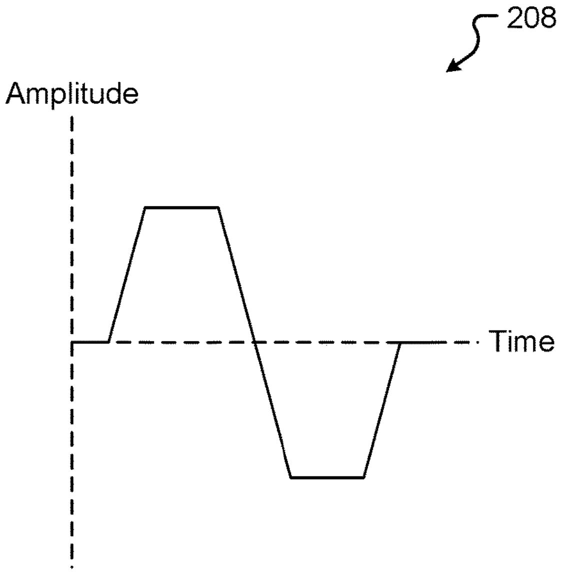
Figure 2D:
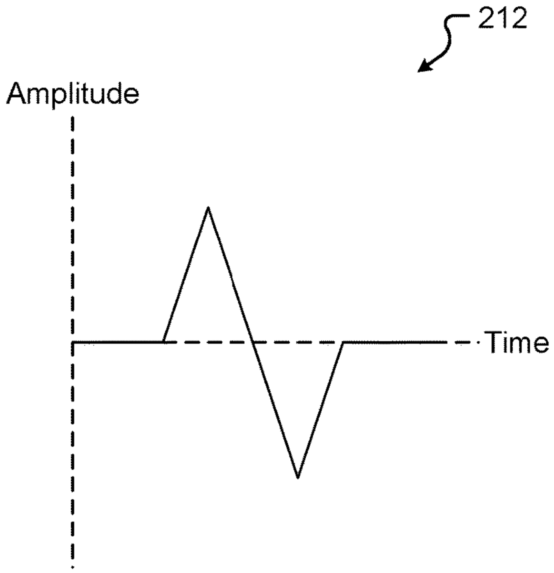

A waveform for the low frequency signal to provide the blocking may be different shapes. For example, FIG. 2A depicts a first waveform shape 200 that can be used to provide the blocking therapy, such as a square wave. FIG. 2B depicts a second waveform shape 204 that can be used to provide the blocking therapy, such as a sinusoidal wave. FIG. 2C depicts a third waveform shape 208 that can be used to provide the blocking therapy, such as a trapezoidal wave. FIG. 2D depicts a fourth waveform shape 212 that can be used to provide the blocking therapy, such as a triangular wave. While FIGS. 2A-2D illustrate possible waveform shapes that can be used to provide the blocking effect of the neuromodulation therapy described herein, additional waveform shapes may be used to provide the blocking therapy, as long as the waveform shapes are charge balanced. The low frequency waveforms may be less energy intensive than higher frequency waveforms that can provide the blocking.

In some examples, the low frequency waveforms may have a same charge density as each other, regardless of the specific frequency or specific waveform shape is used to apply the stimulation/block therapy. For example, a current (e.g., a signal) may be applied to an anatomical element of the patient using a first waveform of a set of waveforms that an implantable pulse generator is capable of generating, where each of the set of waveforms includes a same charge density. Additionally, a waveform for the low frequency signal may include varying pulse widths from 0.05 ms to 10 ms.

Figure 3:
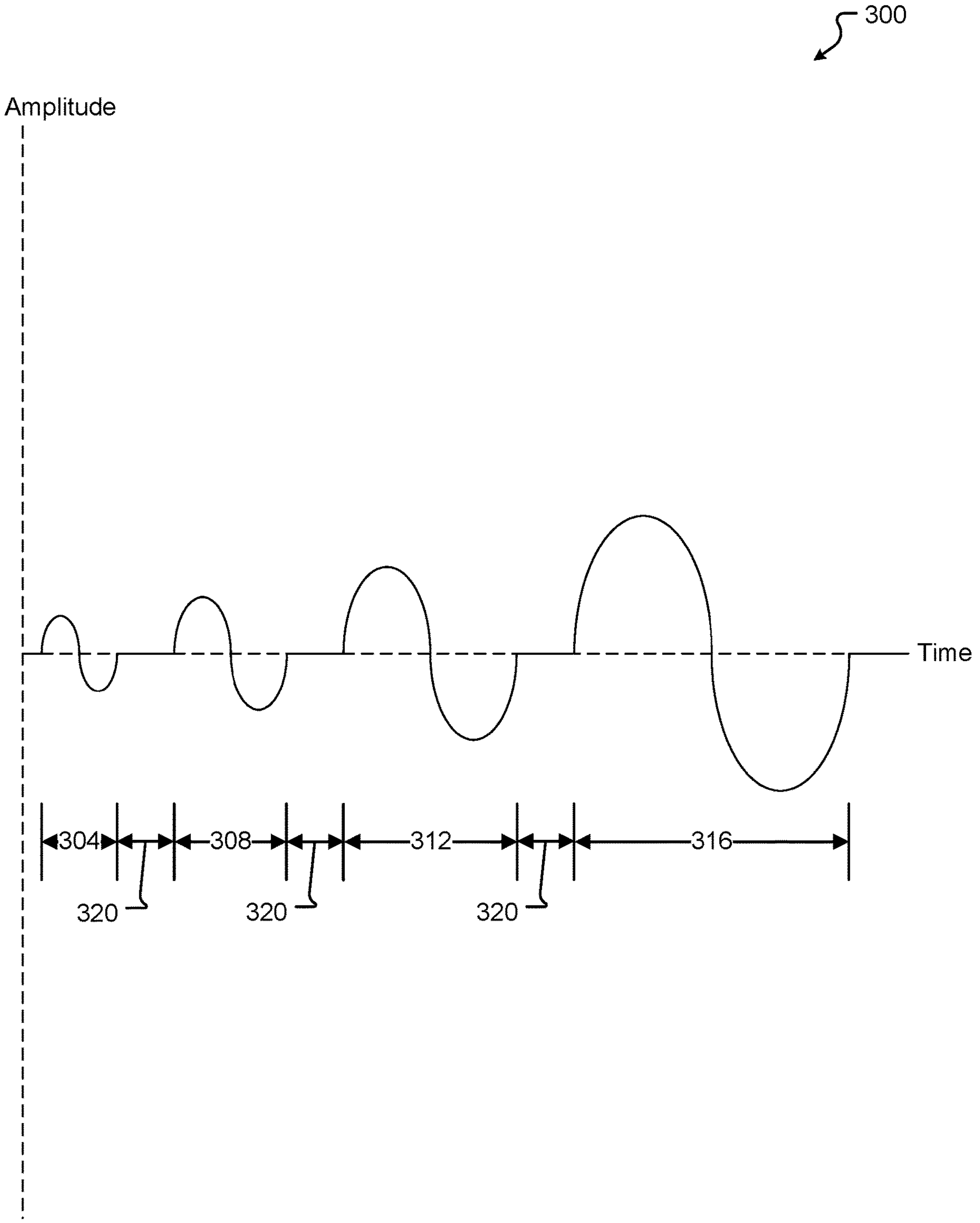
FIG. 3 is a waveform modulation technique according to at least one embodiment of the present disclosure.

FIG. 3 depicts a waveform modulation technique 300 that supports neuromodulation techniques to create a nerve blockage with a combination stimulation/block therapy for glycemic control as described herein. In some examples, the waveform modulation technique 300 may be used to support glycemic control in the patient. For example, the waveform modulation technique 300 may include slowly increasing an amplitude and/or frequency of a pulse (e.g., a current) that provides the blocking to the vagus nerve (e.g., at the hepatic vagal trunk or the anterior sub diaphragmatic vagal trunk at the hepatic branching point of the vagus nerve), such a desired shape for the pulse is achieved. In some examples, the waveform modulation technique 300 may be used to create a different pulse shape than an initial pulse shape of a first waveform (e.g., as modulated by time and amplitude) such that a desired effect is achieved (e.g., the desired shape of the pulse). In some examples, the charge density (e.g., the amount of charge that is delivered to the vagus nerve) is neutral (e.g., the pulse with which the current/charge is applied is balanced in a positive and negative sense). In some examples, the waveform modulation technique 300 may occur over a period of time until the desired shape for the pulse is achieved.

To achieve the blocking portion of the stimulation/block therapy, an implantable pulse generator may begin the therapy by transmitting a first waveform 304 that has a minimal amplitude and/or frequency. Subsequently, the implantable pulse generator may increase a frequency, an amplitude, or both of the first waveform 304 incrementally (e.g., over a specified period of time) until a desired shape is generated to provide a needed glycemic response in the patient. For example, the frequency and/or amplitude of the first waveform 304 may be increased to generate a second waveform 308. Similarly, the frequency and/or amplitude of the second waveform 308 may be increased to generate a third waveform 312, and the frequency and/or amplitude of the third waveform 312 may be increased to generate a fourth waveform 316. The fourth waveform 316 may represent the desired shape for providing the blocking portion of the stimulation/block therapy. That is, the frequency and/or amplitude of the fourth waveform 316 may achieve a desired result on a glycemic response of the patient (e.g., blocking production of excess glucose) without using high energy waveforms for extended periods of time. In some examples, the first waveform 304, the second waveform 308, the third waveform 312, and the fourth waveform 316 may be a same or substantially similar waveform that have one or more parameters (e.g., amplitude, frequency, etc.) thereof adjusted.

In some examples, between each modulation (e.g., between adjusting parameters of each waveform), a time gap 320 may occur. For example, the time gap 320 may occur between applying or generating the current using the first waveform 304 and the second waveform 308, between the second waveform 308 and the third waveform 312, between the third waveform 312 and the fourth waveform 316, etc. While shown as having a same duration for each instance of the time gap 320, the time gap 320 may differ in duration between each modulation of the pulse/current (e.g., adjusting the amplitude, frequency, etc.) to generate each corresponding waveform.

Figure 4:
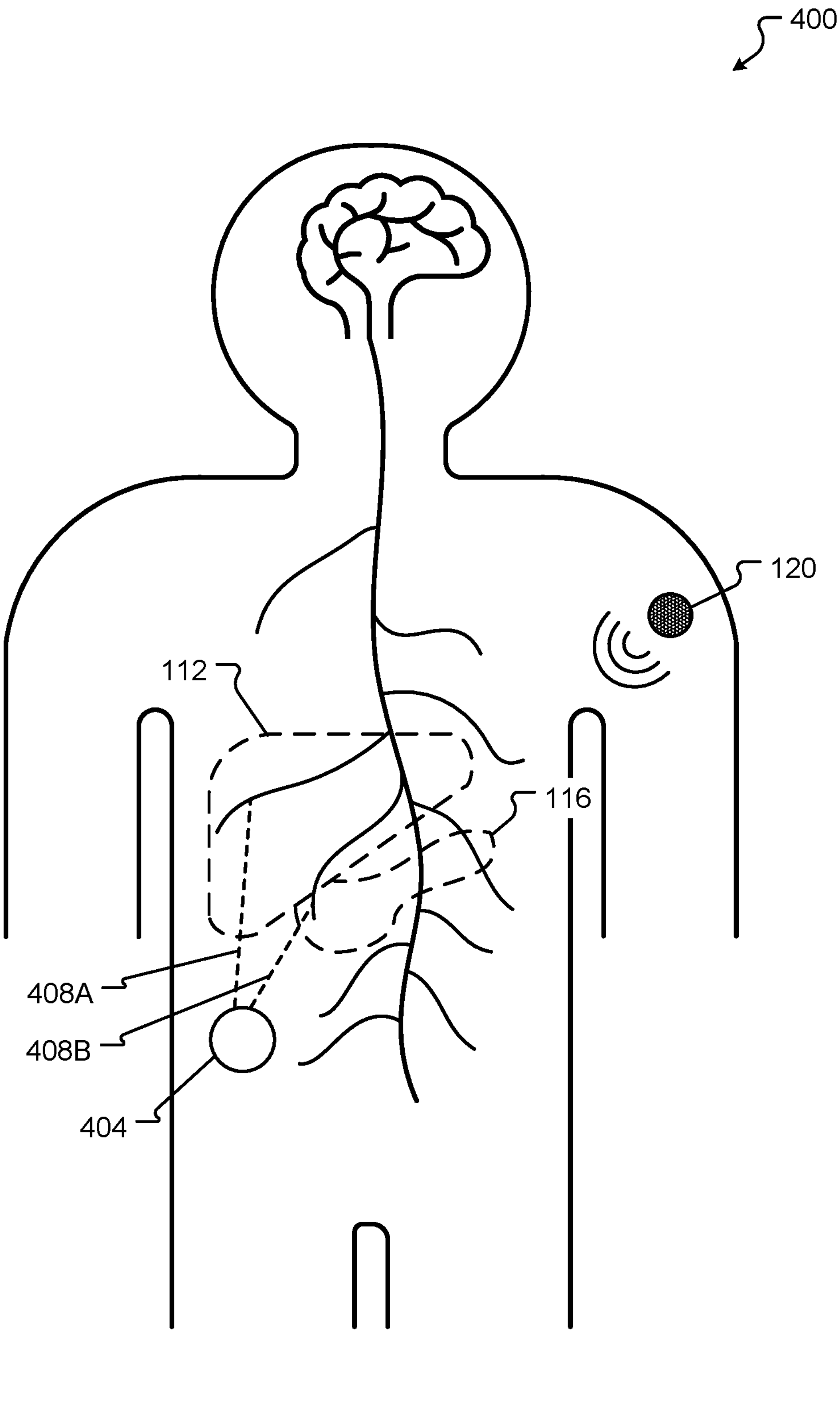
FIG. 4 is a micropump system according to at least one embodiment of the present disclosure.

FIG. 4 depicts a micropump system 400 that supports creating a nerve blockage for glycemic control as described herein. For example, the techniques described herein may use a pharmacologic injection (e.g., via a micropump inserted in or located on the patient) to provide the blocking therapy. Pharmacologic blockade is a technique used to block pain in a patient. Subsequently, as described herein, a micropump 404 (e.g., or other type of device) may be used to achieve a pharmacologic blockade via local delivery of an agent in the proximity of the sub diaphragmatic vagal trunk at the hepatic branching point (e.g., of the vagus nerve). For example, the micropump 404 may be configured to deliver a pharmacological agent to an anatomical element. In some examples, the micropump 404 may be implanted within the patient or may be otherwise disposed in or on the patient, such that pharmacological agents are able to be injected directly from the micropump 404 to the patient.

In some examples, the techniques for inducing the block may include delivering glucose (e.g., via the micropump 404 or another type of device) to the liver of the patient by delivering to sensing elements of the liver in a microenvironment or by delivering to receptors on the liver surface to circumvent a systemic response. Accordingly, delivering glucose to the liver may block the liver from adding more glucose but also causes other neural pathways to release glycogen (e.g., causes the liver to "believe" it is in a high energy environment). Additionally or alternatively, the techniques for inducing the block may include delivering insulin (e.g., via the micropump 404 or another type of device) into the patient, such that the insulin decreases glucose levels in the patient and/or blocks the liver from producing more glucose. Accordingly, in some examples, the pharmacological agent delivered by the micropump 404 may include glucose, insulin, or another agent that, when delivered, reduces glycemic levels in the patient (e.g., provides glycemic control). Additionally or alternatively, the pharmacological agent may mimic actions associated with insulin and/or glucagon (e.g., or a different hormone).

In some examples, the micropump 404 may include a round implantable pump (e.g., as illustrated in the example of FIG. 4) with two delivery catheters 408 that are configured to deliver the pharmacological agent to the anatomical element of the patient (e.g., vagal nerve trunks of the patient). For example, a first delivery catheter 408A may be connected to or may deliver the pharmacological agent in the vicinity of a first vagal trunk of the patient and/or to or in the vicinity of a first organ 112 (e.g., such as the first organ 112 as described with reference to FIG. 1). Additionally, a second delivery catheter 408B may be connected to or may deliver the pharmacological agent in the vicinity of a second vagal trunk of the patient and/or to or in the vicinity of a second organ 116 (e.g., such as the second organ 116 as described with reference to FIG. 1). Additionally or alternatively, while the respective vagal trunks are shown as being connected to the corresponding organs of the patient as described, the vagal trunks to which the delivery catheters 408 deliver the pharmacological agent may be connected to the other organ (e.g., the first vagal trunk is connected to the second organ 116 and the second vagal trunk is connected to the first organ 112) or may deliver the pharmacological agent to different organs of the patient.

In some examples, the micropump system 400 may be used independently of the implantable pulse generator, electrode, and neuromodulation techniques previously described. For example, a patient may use the micropump 404 alone to the provide the pharmacological blockade described with reference to FIG. 4. The pharmacological blockade may provide a similar result as the electrical stimulation/block therapy described with reference to FIGS. 1-3 to achieve glycemic control in the patient without applying a current to an anatomical element in the patient. Additionally or alternatively, the micropump system 400 may be used in coordination with the electrical stimulation/block therapy described herein. For example, the micropump 404 may refrain from delivering a pharmacological agent while the electrical stimulation/block therapy is being applied, or the electrical stimulation/block therapy may be reduced (e.g., the implantable pulse generator or the deice 104 as described with reference to FIG. 1 provides a less-intensive current) if the micropump 404 is delivering the pharmacological agent.

In some examples, the micropump system 400 may also optionally include the glucose sensor 120 (e.g., as described with reference to FIG. 1) that communicates (e.g., wirelessly) with the micropump 404 (e.g., and/or one or more processors, control devices, etc., not explicitly shown in the example of FIG. 4) to achieve better glycemic control in the patient as described herein. For example, the glucose sensor 120 may continuously monitor glucose levels of the patient, such that if the glucose sensor 120 determines glucose levels are outside a normal or desired range for the patient (e.g., glucose levels are too high or too low in the patient), the glucose sensor 120 may communicate that glucose levels are outside the normal or desired range to the micropump 404 (e.g., via the one or more processors) to signal for the micropump 404 to deliver the pharmacological agent to the anatomical element described herein to adjust glucose levels in the patient (e.g., mute the glycemic response to lower glucose levels in the patient, block insulin production in the patient as a possible technique to raise glucose levels in the patient, etc.).

Figure 5:
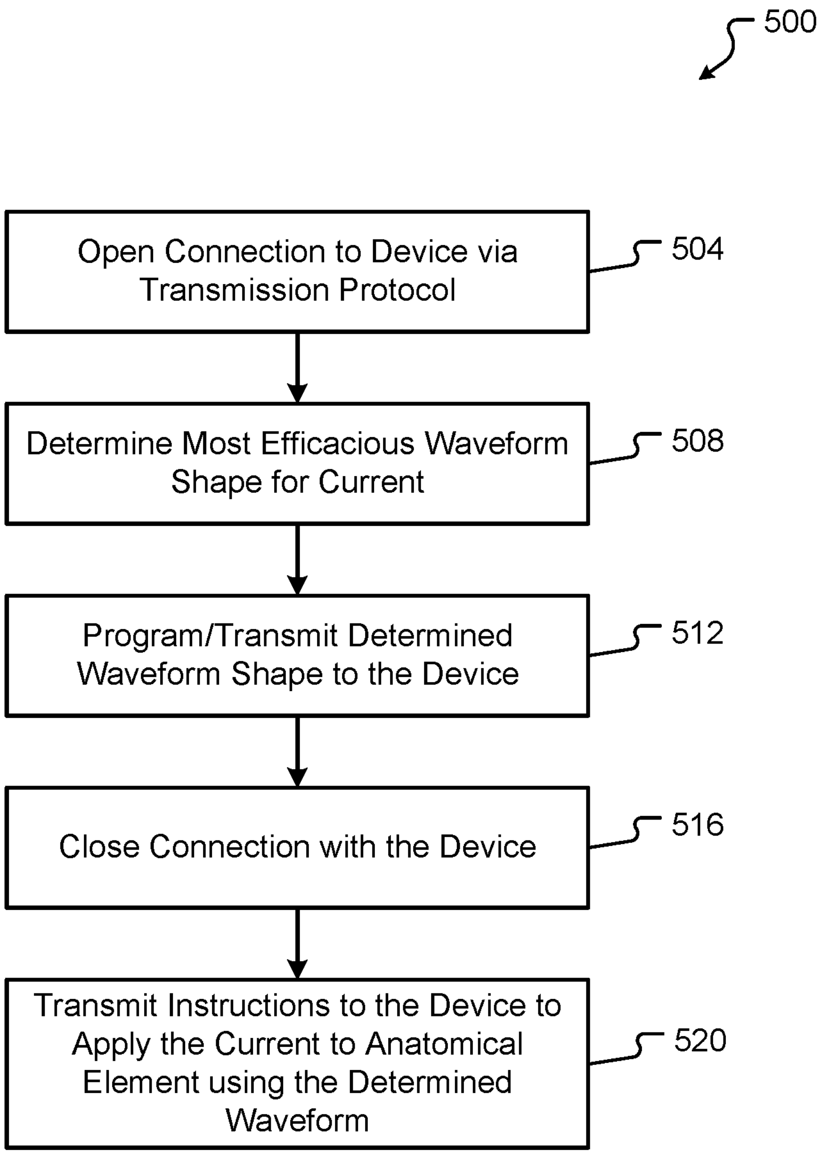
FIG. 5 is a flowchart according to at least one embodiment of the present disclosure.

FIG. 5 depicts a method 500 that may be used, for example, to apply a current to an anatomical element of a patient (e.g., neuromodulation techniques) to create a nerve blockage with a combination stimulation/block therapy for glycemic control as described herein. For example, applying the current to the anatomical element may be used to provide a stimulation to the anatomical element of the patient.

The method 500 (and/or one or more steps thereof) may be carried out or otherwise performed, for example, by at least one processor. The at least one processor may be the same as or similar to the processor(s) of the device 104 described above. The at least one processor may be part of the device 104 (such as an implantable pulse generator) or part of a control unit in communication with the device 104. A processor other than any processor described herein may also be used to execute the method 500. The at least one processor may perform the method 500 by executing elements stored in a memory (such as a memory in the device 104 as described above or a control unit). The elements stored in the memory and executed by the processor may cause the processor to execute one or more steps of a function as shown in method 500. One or more portions of a method 500 may be performed by the processor executing any of the contents of memory, such as providing a stimulation/block therapy and/or any associated operations as described herein.

The method 500 comprises opening a connection via a transmission protocol (step 504). For example, the connection may be made between the at least one processor described above and a device. As described herein, the device may be configured to generate a current that is to be applied to an anatomical element of a patient, where the current is configured to achieve glycemic control in the patient. For example, the device may be the device 104 as described with reference to FIG. 1 (e.g., an implantable pulse generator, implantable neurostimulator, etc.). The method 500 also comprises determining a most efficacious waveform shape for the current that is to be applied to the anatomical element via a clinical programmer (step 508). For example, the most efficacious waveform shape may be determined based on a glycemic response of the patient (e.g., a previously recorded glycemic response when a same or different current was applied to the anatomical element), patient comfort, etc. Subsequently, the method 500 comprises programming or transmitting transmit a final waveform shape to the device (step 512). For example, the final waveform shape may include the most efficacious waveform shape determined previously at step 508. The method 500 also comprises closing the connection (e.g., between the at least one processor and the device (step 516).

Based on the steps 504 to 516, the at least one processor may determine a waveform for applying the current to the anatomical element of the patient. For example, the waveform may include a frequency between 0.1 and 20 Hz (e.g., low-frequency blockade). Additionally or alternatively, the waveform may include a biphasic pulse (e.g., a preceding negative pulse immediately followed by a positive one or vice versa). In some examples, as described with reference to FIGS. 1 and 2A-2D, the waveform may include a square wave shape, a trapezoidal wave shape, a sinusoidal wave shape, or another wave shape that is charge balanced. Additionally, the waveform may be selected or determined from a set of waveforms that an implantable pulse generator is capable of generating, where each waveform in the set of waveforms include a same charge density. For example, each of the waveforms, regardless of shape and/or frequency, may generate or otherwise deliver a same charge as the other waveforms in the set of waveforms.

The method 500 also comprises transmitting instructions to the device (e.g., an implantable pulse generator, such as the device 104 as described with reference to FIG. 1) to apply the current generated using the determined waveform to the anatomical element of the patient (e.g., a celiac vagal trunk and/or a hepatic vagal trunk of the patient) via a plurality of electrodes of an electrode device connected to the device (step 520). For example, the electrode device may include the wires 108 and cuff electrodes (e.g., plurality of electrodes) as described with reference to FIG. 1. In some examples, the electrode device may include a body and the plurality of electrodes that are disposed on the body and configured to apply the current to the anatomical element.

The present disclosure encompasses embodiments of the method 500 that comprise more or fewer steps than those described above, and/or one or more steps that are different than the steps described above.

Figure 6:
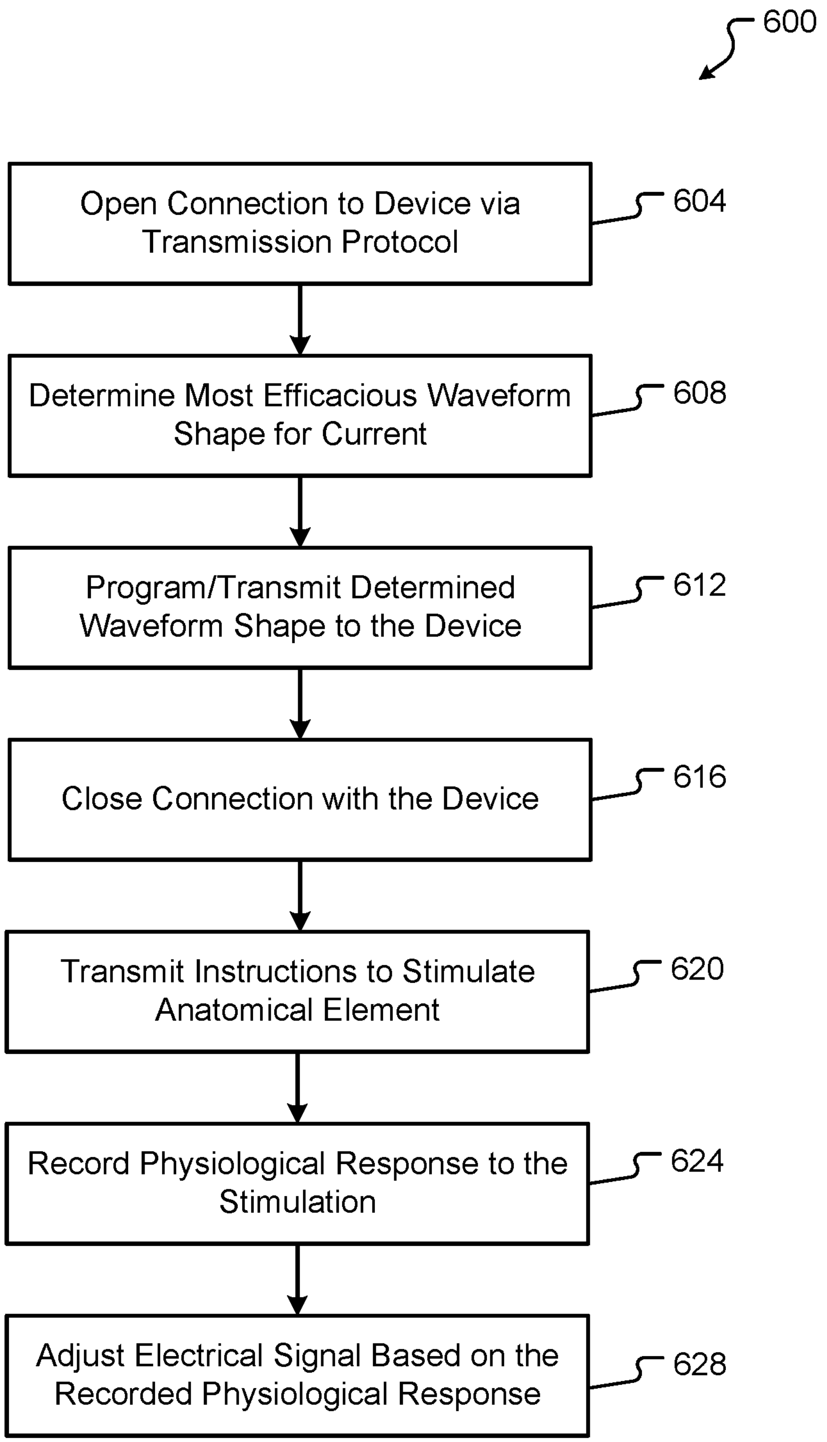
FIG. 6 is a flowchart according to at least one embodiment of the present disclosure.

FIG. 6 depicts a method 600 that may be used, for example, to modulate a waveform when applying a current to an anatomical element of a patient (e.g., neuromodulation techniques) to create a nerve blockage with a combination stimulation/block therapy for glycemic control as described herein. For example, modulating the waveform when applying the current to the anatomical element may be used, in part, to provide a stimulation to the anatomical element of the patient.

The method 600 (and/or one or more steps thereof) may be carried out or otherwise performed, for example, by at least one processor. The at least one processor may be the same as or similar to the processor(s) of the device 104 described above. The at least one processor may be part of the device 104 (such as an implantable pulse generator) or part of a control unit in communication with the device 104. A processor other than any processor described herein may also be used to execute the method 600. The at least one processor may perform the method 600 by executing elements stored in a memory (such as a memory in the device 104 as described above or a control unit). The elements stored in the memory and executed by the processor may cause the processor to execute one or more steps of a function as shown in method 600. One or more portions of a method 600 may be performed by the processor executing any of the contents of memory, such as providing a stimulation/block therapy and/or any associated operations as described herein.

The method 600 comprises determining a waveform for applying a current to an anatomical element of a patient via a device (e.g., implantable pulse generator, device 104, etc.). For example, the method 600 may include opening a connection via a transmission protocol (step 604), determining a most efficacious waveform shape for the current that is to be applied to the anatomical element via a clinical programmer (step 608), programming or transmitting transmit a final waveform shape to the device (step 612), and closing the connection (step 616). The method 600 also comprises transmitting instructions to the device (e.g., implantable pulse generator, device 104, etc.) to apply the current using the determined waveform to the anatomical element of the patient (e.g., a celiac vagal trunk and/or a hepatic vagal trunk of the patient) via a plurality of electrodes of an electrode device connected to the device (step 620). For example, the instructions to apply the current to the anatomical element may include instructions to stimulate the anatomical element. Steps 604, 608, 612, 616, and 620 may implement aspects of steps 504, 508, 512, 516, and 520, respectively, as described with reference to FIG. 5.

The method 600 also comprises recording a physiological response of the patient (step 624) based on the stimulation applied to the anatomical element according to the instructions transmitted at step 620 using the determined waveform from steps 604-616. For example, the physiological response may include a glycemic response of the patient when the current/stimulation is applied to the anatomical element. Accordingly, the physiological response may be compared to an expected or desired glycemic response for the patient. The desired glycemic response as described herein may correspond to a glycemic response the patient is satisfied and comfortable with and/or a glycemic response that includes a peak post prandial glycemic level that stays within an acceptable range (e.g., glycemic levels above this range may cause harm to the patient over time and glycemic levels below this range may cause hypoglycemia in the patient).

The method 600 also comprises transmitting instructions to the device to increase a frequency, an amplitude, or both of the waveform determined/selected to be applied to the anatomical element incrementally over a specified period of time (step 624). For example, as described with reference to FIG. 3, the frequency, the amplitude, or both of the waveform may be incrementally increased over time to generate a desired shape for the waveform to support glycemic control in the patient. In some examples, the instructions to increase the frequency, the amplitude, or both of the waveform may be transmitted to the device based on the recorded physiological response made for step 624. For example, if the recorded physiological response is different than the expected or desired glycemic response, the waveform may be adjusted (e.g., modulated) as described herein until the expected or desired glycemic response (e.g., with a desired/final waveform) is achieved.

The present disclosure encompasses embodiments of the method 600 that comprise more or fewer steps than those described above, and/or one or more steps that are different than the steps described above.

Figure 7:
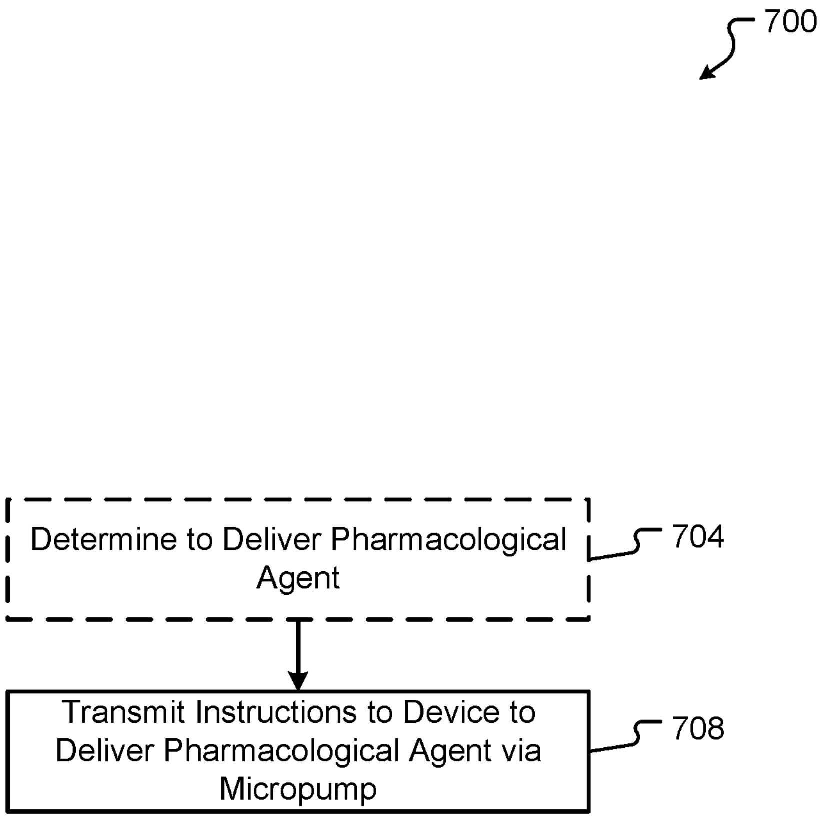
FIG. 7 is a flowchart according to at least one embodiment of the present disclosure.

FIG. 7 depicts a method 700 that may be used, for example, for delivering a pharmacological agent to provide a pharmacological blockade at an anatomical element of a patient.

The method 700 (and/or one or more steps thereof) may be carried out or otherwise performed, for example, by at least one processor. The at least one processor may be the same as or similar to the processor(s) of the device 104 described above. The at least one processor may be part of the device 104 (such as an implantable pulse generator) or part of a control unit in communication with the device 104. A processor other than any processor described herein may also be used to execute the method 700. The at least one processor may perform the method 700 by executing elements stored in a memory (such as a memory in the device 104 as described above or a control unit). The elements stored in the memory and executed by the processor may cause the processor to execute one or more steps of a function as shown in method 700. One or more portions of a method 700 may be performed by the processor executing any of the contents of memory, such as providing a stimulation/block therapy and/or any associated operations as described herein.

The method 700 comprises determining to deliver a pharmacological agent to the anatomical element of the patient (step 704). For example, a device may determine to deliver the pharmacological agent based on glucose levels in the patient rising, the patient having just eaten a meal, or another situation not explicitly described herein. The device that determines to deliver the pharmacological agent may include the processor or another computing device that can receive inputs and transmit instructions based on the inputs.

The method 700 also comprises transmitting instructions to a device (e.g., a micropump 404 as described with reference to FIG. 4 or another device) to deliver the pharmacological agent to the anatomical element (e.g., via the micropump 404 or another device), where the pharmacological agent blocks a physiological response of the anatomical element (step 708). In some examples, the physiological response may include the anatomical element conventionally increasing glucose production in the patient if the pharmacological agent did not block such activity. For example, the pharmacological agent may block the liver from producing glucose (e.g., a physiological response of the liver would be to produce glucose after a meal is digested by the patient) and stimulates neural pathways of the patient to release glucagon. In some examples, the pharmacological agent may mimic actions of a hormone of the patient, such as insulin or glucagon.

In some examples, the pharmacological agent may be delivered to a hepatic vagal trunk of the patient to block glucose production in the patient. Additionally or alternatively, the pharmacological agent may be delivered to the liver and/or receptors on the surface of the liver to block glucose production at the liver. In some examples, the pharmacological agent may include glucose, glucagon, insulin, or another agent that blocks glucose production when delivered to an anatomical element of the patient (e.g., and/or mimics actions associated with one of those hormones).

The present disclosure encompasses embodiments of the method 700 that comprise more or fewer steps than those described above, and/or one or more steps that are different than the steps described above.

As noted above, the present disclosure encompasses methods with fewer than all of the steps identified in FIGS. 5, 6, and 7 (and the corresponding description of the methods 500, 600, and 700), as well as methods that include additional steps beyond those identified in FIGS. 5, 6, and 7 (and the corresponding description of the methods 500, 600, and 700). The present disclosure also encompasses methods that comprise one or more steps from one method described herein, and one or more steps from another method described herein. Any correlation described herein may be or comprise a registration or any other correlation.

Figure 8:
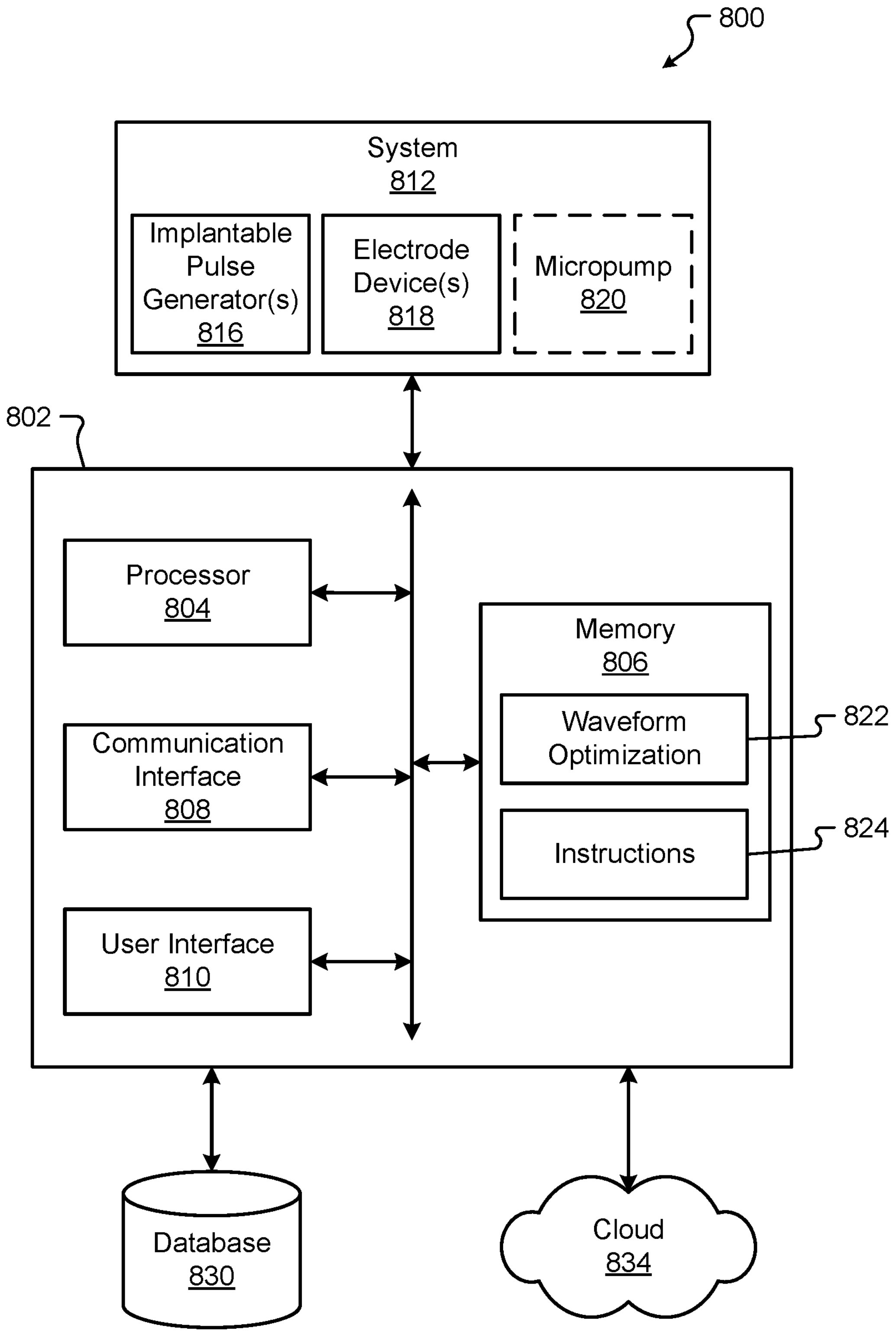
FIG. 8 is a block diagram of a system according to at least one embodiment of the present disclosure.

FIG. 8 depicts a block diagram of a system 800 according to at least one embodiment of the present disclosure is shown. In some examples, the system 800 may implement aspects of or may be implemented by aspects of FIGS. 1-7 as described herein. For example, the system 800 may be used with an implantable pulse generator 816 and/or an electrode device 818, and/or carry out one or more other aspects of one or more of the methods disclosed herein. The implantable pulse generator 816 may represent an example of the device 104 or a component of the device 104 as described with reference to FIG. 1, where the electrode device 818 may represent the wires 108 and corresponding electrodes/cuff electrodes as described with reference to FIG. 1. Additionally or alternatively, the system 800 may be used with a micropump 820 and/or may carry out one or more other aspects of one or more of the methods disclosed herein. The micropump 820 may represent an example of the micropump 404 as described with reference to FIG. 4. The system 800 comprises a computing device 802, a system

812, a database 830, and/or a cloud or other network 834. Systems according to other embodiments of the present disclosure may comprise more or fewer components than the system 800. For example, the system 800 may not include one or more components of the computing device 802, the database 830, and/or the cloud 834.

The system 812 may comprise the implantable pulse generator 816 and the electrode device 818. As previously described, the implantable pulse generator 816 may be configured to generate a current, and the electrode device 818 may comprise a plurality of electrodes configured to apply the current to an anatomical element. Additionally or alternatively, the system 812 may comprise the micropump 820 that is configured to deliver a pharmacological agent to the anatomical element to block a physiological response of the anatomical element (e.g., the micropump 820 provides a pharmacological blockage by delivering the pharmacological agent to block the anatomical element from producing excess glucose in the patient). The system 812 may communicate with the computing device 802 to receive instructions such as instructions 824 for applying a current to the anatomical element and/or delivering the pharmacological agent to the anatomical element. The system 812 may also provide data (such as data received from an electrode device 818 capable of recording data), which may be used to optimize the electrodes of the electrode device 818 and/or to optimize parameters of the current generated by the implantable pulse generator 816.

The computing device 802 comprises a processor 804, a memory 806, a communication interface 808, and a user interface 810. Computing devices according to other embodiments of the present disclosure may comprise more or fewer components than the computing device 802.

The processor 804 of the computing device 802 may be any processor described herein or any similar processor. The processor 804 may be configured to execute instructions 824 stored in the memory 806, which instructions may cause the processor 804 to carry out one or more computing steps utilizing or based on data received from the system 812, the database 830, and/or the cloud 834.

The memory 806 may be or comprise RAM, DRAM, SDRAM, other solid-state memory, any memory described herein, or any other tangible, non-transitory memory for storing computer-readable data and/or instructions. The memory 806 may store information or data useful for completing, for example, any steps of the methods 500, 600, and/or 700 described herein, or of any other methods. The memory 806 may store, for example, instructions and/or machine learning models that support one or more functions of the system 812. For instance, the memory 806 may store content (e.g., instructions and/or machine learning models) that, when executed by the processor 804, enable electrode(s) optimization 820.

The waveform optimization 822 enables the processor 804 to determine an optimal waveform to use when applying the current to the anatomical element of the patient. For example, as described with reference to FIGS. 1-3, the current may be applied to the anatomical element using a waveform of any given shape that is biphasic and charge-balanced and has a same charge density as other waveforms that the implantable pulse generator 816 is capable of generating. The waveform optimization 822 also enables the processor 804 to apply the current using the optimal waveform to the anatomical element of the patient. The waveform optimization 822 also further enables the processor 804 to generate instructions 824 which may comprise, for example, current parameters for the implantable pulse generator 816 to generate a current using the determined waveform. Additionally or alternatively, the instructions 824 may enable the micropump 820 to deliver the pharmacological agent to the anatomical element.

Content stored in the memory 806, if provided as in instruction, may, in some embodiments, be organized into one or more applications, modules, packages, layers, or engines. Alternatively or additionally, the memory 806 may store other types of content or data (e.g., machine learning models, artificial neural networks, deep neural networks, etc.) that can be processed by the processor 804 to carry out the various method and features described herein. Thus, although various contents of memory 806 may be described as instructions, it should be appreciated that functionality described herein can be achieved through use of instructions, algorithms, and/or machine learning models. The data, algorithms, and/or instructions may cause the processor 804 to manipulate data stored in the memory 806 and/or received from or via the system 812, the database 830, and/or the cloud 834.

The computing device 802 may also comprise a communication interface 808. The communication interface 808 may be used for receiving data (for example, data from an electrode device 818 capable of recording data) or other information from an external source (such as the system 812, the database 830, the cloud 834, and/or any other system or component not part of the system 800), and/or for transmitting instructions, images, or other information to an external system or device (e.g., another computing device 802, the system 812, the database 830, the cloud 834, and/or any other system or component not part of the system 800). The communication interface 808 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 808 may be useful for enabling the device 802 to communicate with one or more other processors 804 or computing devices 802, whether to reduce the time needed to accomplish a computing-intensive task or for any other reason.

The computing device 802 may also comprise one or more user interfaces 810. The user interface 810 may be or comprise a keyboard, mouse, trackball, monitor, television, screen, touchscreen, and/or any other device for receiving information from a user and/or for providing information to a user. The user interface 810 may be used, for example, to receive a user selection or other user input regarding any step of any method described herein. Notwithstanding the foregoing, any required input for any step of any method described herein may be generated automatically by the system 800 (e.g., by the processor 804 or another component of the system 800) or received by the system 800 from a source external to the system 800. In some embodiments, the user interface 810 may be useful to allow a surgeon or other user to modify instructions to be executed by the processor 804 according to one or more embodiments of the present disclosure, and/or to modify or adjust a setting of other information displayed on the user interface 810 or corresponding thereto.

Although the user interface 810 is shown as part of the computing device 802, in some embodiments, the computing device 802 may utilize a user interface 810 that is housed separately from one or more remaining components of the computing device 802. In some embodiments, the user interface 810 may be located proximate one or more other components of the computing device 802, while in other embodiments, the user interface 810 may be located remotely from one or more other components of the computer device 802.

Though not shown, the system 800 may include a controller, though in some embodiments the system 800 may not include the controller. The controller may be an electronic, a mechanical, or an electro-mechanical controller. The controller may comprise or may be any processor described herein. The controller may comprise a memory storing instructions for executing any of the functions or methods described herein as being carried out by the controller. In some embodiments, the controller may be configured to simply convert signals received from the computing device 802 (e.g., via a communication interface 108) into commands for operating the system 812 (and more specifically, for actuating the implantable pulse generator 816 and/or the electrode device 818). In other embodiments, the controller may be configured to process and/or convert signals received from the system 812. Further, the controller may receive signals from one or more sources (e.g., the system 812) and may output signals to one or more sources.

The database 830 may store information such as patient data, results of a stimulation and/or blocking procedure, stimulation and/or blocking parameters, current parameters, electrode parameters, etc. The database 830 may be configured to provide any such information to the computing device 802 or to any other device of the system 800 or external to the system 800, whether directly or via the cloud 834. In some embodiments, the database 830 may be or comprise part of a hospital image storage system, such as a picture archiving and communication system (PACS), a health information system (HIS), and/or another system for collecting, storing, managing, and/or transmitting electronic medical records.

The cloud 834 may be or represent the Internet or any other wide area network. The computing device 802 may be connected to the cloud 834 via the communication interface 808, using a wired connection, a wireless connection, or both. In some embodiments, the computing device 802 may communicate with the database 830 and/or an external device (e.g., a computing device) via the cloud 834.

The system 800 or similar systems may be used, for example, to carry out one or more aspects of any of the methods 500, 600, and/or 700 as described herein. The system 800 or similar systems may also be used for other purposes.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for stimulating an anatomical element of a patient, comprising:

an implantable pulse generator configured to generate a first waveform with a neutral current;

an electrode device electrically coupled to the implantable pulse generator, the electrode device comprising a plurality of electrodes configured for placement on or around a first anatomical element of the patient;

a processor; and a memory storing data for processing by the processor, the data, when processed, causes the processor to:

transmit instructions to cause the implantable pulse generator to:

generate the first waveform with the neutral current to have an incrementally increasing amplitude; and apply the generated first waveform with the neutral current and with the incrementally increased amplitude to the first anatomical element of the patient via the plurality of electrodes of the electrode device to manipulate a circadian cycle of a liver of the patient by downregulating a first nervous system tone associated with the first anatomical element to match a second nervous system tone that represents nighttime activity of the liver which causes a glycemic response in the patient.

2. The system of claim 1, wherein the first anatomical element comprises a celiac vagal trunk and a hepatic vagal trunk of the patient.

3. The system of claim 2, wherein the first waveform comprises a frequency between 0.1 and 20 hertz (Hz).

4. The system of claim 3, wherein the first waveform comprises a biphasic pulse.

5. The system of claim 4, wherein the first waveform comprises a square wave shape, a trapezoidal wave shape, a sinusoidal wave shape, or another wave shape that is charge balanced.

6. The system of claim 3, wherein the memory stores further data for processing by the processor that, when processed, causes the processor to:

transmit instructions to the implantable pulse generator to incrementally increase the frequency, the amplitude, or both of the first waveform when applying the neutral current.

7. The system of claim 6, wherein the frequency, the amplitude, or both of the first waveform are incrementally increased over time to generate a desired shape for the first waveform.

8. The system of claim 1, wherein the data stored in the memory that, when processed causes the processor to transmit instructions to the implantable pulse generator to apply the neutral current using the first waveform further causes the system to:

transmit instructions to the implantable pulse generator to apply a pattern of stimulation pulses to the first anatomical element to simulate a physiological neuron spiking behavior at the first anatomical element, wherein the first waveform comprises the pattern of stimulation pulses.

9. The system of claim 8, wherein the first waveform comprises a standard shape that is determined based at least in part on a plurality of patient studies, common physiological patterns, or a combination thereof.

10. The system of claim 8, wherein the first waveform comprises a shape that is determined based at least in part on observing signaling on the first anatomical element at different stages of a metabolic cycle of the patient.

11. The system of claim 8, wherein the pattern of stimulation pulses is regular or non-regular.

12. A system for stimulating an anatomical element of a patient, comprising:

an implantable pulse generator configured to generate a first waveform with a neutral current;

an electrode device comprising:

a body; and a plurality of electrodes disposed on the body and configured to apply the neutral current to a first anatomical element;

a processor; and a memory storing data for processing by the processor, the data, when processed, causes the processor to:

transmit instructions to cause the implantable pulse generator to:

generate the first waveform with the neutral current to have an incrementally increasing amplitude; and apply the generated first waveform with the neutral current and with the incrementally increased amplitude to the first anatomical element of the patient via the plurality of electrodes of the electrode device to manipulate a circadian cycle of a liver of the patient by downregulating a first nervous system tone associated with the first anatomical element to match a second nervous system tone that represents nighttime activity of the liver which causes a glycemic response in the patient.

13. The system of claim 12, wherein the anatomical element comprises a celiac vagal trunk and a hepatic vagal trunk of the patient.

14. An implantable pulse generator to stimulate an anatomical element of a patient, comprising:

a processor; and a memory storing data for processing by the processor, the data, when processed, causes the processor to:

generate a first waveform with a neutral current to have an incrementally increasing amplitude; and apply, via one or more electrodes, the generated first waveform with the neutral current and with the incrementally increased amplitude to a first anatomical element of the patient to manipulate a circadian cycle of a liver of the patient by downregulating a first nervous system tone associated with the first anatomical element to match a second nervous system tone that represents nighttime activity of the liver which causes a glycemic response in the patient.

15. The implantable pulse generator of claim 14, wherein the first anatomical element comprises a celiac vagal trunk and a hepatic vagal trunk of the patient.

16. The implantable pulse generator of claim 15, wherein the first waveform comprises a frequency between 0.1 and 20 hertz (Hz).

17. The implantable pulse generator of claim 16, wherein the first waveform comprises a biphasic pulse.

18. The implantable pulse generator of claim 17, wherein the first waveform comprises a square wave shape, a trapezoidal wave shape, a sinusoidal wave shape, or another wave shape that is charge balanced.

* * * * *